(12) United States Patent
Shannon et al.

(10) Patent No.: US 7,147,752 B2
(45) Date of Patent: Dec. 12, 2006

(54) HYDROPHILIC FIBERS CONTAINING SUBSTANTIVE POLYSILOXANES AND TISSUE PRODUCTS MADE THEREFROM

(75) Inventors: Thomas Gerard Shannon, Neenah, WI (US); Dale Alan Burghardt, Buttes des Morts, WI (US); Lisa Ann Flugge, Appleton, WI (US); David Andrew Moline, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 229 days.

(21) Appl. No.: 10/741,040

(22) Filed: Dec. 19, 2003

(65) Prior Publication Data

US 2004/0144507 A1 Jul. 29, 2004

(30) Foreign Application Priority Data

Dec. 31, 2002 (IT) .......................... TV2002A0161

(51) Int. Cl.
*D21H 17/13* (2006.01)
(52) U.S. Cl. ................ 162/164.4; 162/141; 162/164.6; 428/452; 525/477
(58) Field of Classification Search ..................... None
See application file for complete search history.

(56) References Cited

U.S. PATENT DOCUMENTS

| | | |
|---|---|---|
| 2,757,150 A | 7/1956 | Heritage |
| 3,224,926 A | 12/1965 | Bernardin |
| 3,241,553 A | 3/1966 | Steiger |
| 3,440,135 A | 4/1969 | Chung |
| 3,556,932 A | 1/1971 | Cosica et al. |
| 3,556,933 A | 1/1971 | Williams et al. |
| 3,700,623 A | 10/1972 | Kelm |
| 3,772,076 A | 11/1973 | Keim |
| 3,855,158 A | 12/1974 | Petrovich et al. |
| 3,899,388 A | 8/1975 | Petrovich et al. |
| 4,128,692 A | 12/1978 | Reid |
| 4,129,528 A | 12/1978 | Petrovich et al. |
| 4,147,586 A | 4/1979 | Petrovich et al. |
| 4,222,921 A | 9/1980 | Van Eenam |
| 4,297,860 A | 11/1981 | Pacifici et al. |
| 4,303,471 A | 12/1981 | Laursen |
| 4,357,827 A | 11/1982 | McConnell |
| 4,425,186 A | 1/1984 | May et al. |
| 4,432,833 A | 2/1984 | Breese |
| 4,440,597 A | 4/1984 | Wells et al. |
| 4,469,746 A | 9/1984 | Weisman et al. |
| 4,508,860 A | 4/1985 | Hawes |
| 4,514,345 A | 4/1985 | Johnson et al. |
| 4,528,239 A | 7/1985 | Trokhan |
| 4,529,480 A | 7/1985 | Trokhan |
| 4,556,450 A | 12/1985 | Chuang et al. |
| 4,584,357 A | 4/1986 | Harding |
| 4,600,462 A | 7/1986 | Watt |
| 4,663,220 A | 5/1987 | Wisneski et al. |
| 4,773,110 A | 9/1988 | Hopkins |
| 4,898,642 A | 2/1990 | Moore et al. |
| 4,950,545 A | 8/1990 | Walter et al. |
| 5,057,166 A | 10/1991 | Young, Sr. et al. |
| 5,059,282 A | 10/1991 | Ampulski et al. |
| 5,068,009 A | 11/1991 | Jokinen et al. |
| 5,071,675 A | 12/1991 | Gupta et al. |
| 5,098,522 A | 3/1992 | Smurkoski et al. |
| 5,223,090 A | 6/1993 | Klungness et al. |
| 5,226,992 A | 7/1993 | Morman |
| 5,227,242 A | 7/1993 | Walter et al. |
| 5,230,776 A | 7/1993 | Andersson et al. |
| 5,246,545 A | 9/1993 | Ampulski et al. |
| 5,260,171 A | 11/1993 | Smurkoski et al. |
| 5,275,700 A | 1/1994 | Trokhan |
| 5,300,192 A | 4/1994 | Hansen et al. |
| 5,328,565 A | 7/1994 | Rasch et al. |
| 5,334,289 A | 8/1994 | Trokhan et al. |
| 5,348,620 A | 9/1994 | Hermans et al. |
| 5,353,521 A | 10/1994 | Orloff |
| 5,431,786 A | 7/1995 | Rasch et al. |
| 5,443,899 A | 8/1995 | Barcus et al. |
| 5,489,469 A | 2/1996 | Kobayashi et al. |
| 5,492,759 A | 2/1996 | Eriksson et al. |
| 5,496,624 A | 3/1996 | Stelljes, Jr. et al. |
| 5,500,277 A | 3/1996 | Trokhan et al. |
| 5,501,768 A | 3/1996 | Hermans et al. |
| 5,514,523 A | 5/1996 | Trokhan et al. |
| 5,547,541 A | 8/1996 | Hansen et al. |
| 5,554,467 A | 9/1996 | Trokhan et al. |

(Continued)

FOREIGN PATENT DOCUMENTS

CA      2 370 380 A1      10/2000

(Continued)

OTHER PUBLICATIONS

TAPPI Official Test Method T 402 om-93, "Standard Conditioning and Testing Atmospheres For Paper, Board Pulp Handsheets, and Related Products," published by the TAPPI Press, Atlanta, Georgia, revised 1993, pp. 1-3.

(Continued)

*Primary Examiner*—Marc S. Zimmer
(74) *Attorney, Agent, or Firm*—Gregory E. Croft

(57) ABSTRACT

The present invention is polysiloxane pretreated pulp fibers comprising pulp fibers, and a polysiloxane. The polysiloxane pretreated pulp fibers have a polysiloxane content of about 0.4 percent or greater by weight of dry pulp fibers, a silicone retention factor of about 0.6 or greater, and an initial water drop absorption value of about 180 seconds or less.

31 Claims, 2 Drawing Sheets

U.S. PATENT DOCUMENTS

| | | | |
|---|---|---|---|
| 5,558,873 A | 9/1996 | Funk et al. | |
| 5,566,724 A | 10/1996 | Trokhan et al. | |
| 5,598,642 A | 2/1997 | Orloff et al. | |
| 5,598,643 A | 2/1997 | Chuang et al. | |
| 5,624,790 A | 4/1997 | Trokhan et al. | |
| 5,628,876 A | 5/1997 | Ayers et al. | |
| 5,637,194 A | 6/1997 | Ampulski et al. | |
| 5,656,132 A | 8/1997 | Farrington, Jr. et al. | |
| 5,693,411 A | 12/1997 | Hansen et al. | |
| 5,695,868 A | 12/1997 | McCormack | |
| 5,772,845 A | 6/1998 | Farrington, Jr. et al. | |
| 5,785,813 A | 7/1998 | Smith et al. | |
| 5,814,188 A | 9/1998 | Vinson et al. | |
| 5,843,056 A | 12/1998 | Good et al. | |
| 5,928,470 A | 7/1999 | Shannon | |
| 5,935,383 A | 8/1999 | Sun et al. | |
| 5,981,689 A | 11/1999 | Mitchell et al. | |
| 5,986,166 A | 11/1999 | Mukaida et al. | |
| 6,054,020 A * | 4/2000 | Goulet et al. | 162/112 |
| 6,072,101 A | 6/2000 | Beihoffer et al. | |
| 6,087,448 A | 7/2000 | Mitchell et al. | |
| 6,096,169 A | 8/2000 | Hermans et al. | |
| 6,103,063 A | 8/2000 | Oriaran et al. | |
| 6,110,533 A | 8/2000 | Cote et al. | |
| 6,117,525 A | 9/2000 | Trokhan et al. | |
| 6,121,409 A | 9/2000 | Mitchell et al. | |
| 6,143,135 A | 11/2000 | Hada et al. | |
| 6,149,934 A | 11/2000 | Krzysik et al. | |
| 6,159,591 A | 12/2000 | Beihoffer et al. | |
| 6,168,852 B1 | 1/2001 | Smith, III et al. | |
| 6,194,631 B1 | 2/2001 | Mitchell et al. | |
| 6,222,091 B1 | 4/2001 | Beihoffer et al. | |
| 6,224,714 B1 | 5/2001 | Schroeder et al. | |
| 6,228,506 B1 | 5/2001 | Hosatte et al. | |
| 6,231,719 B1 | 5/2001 | Garvey et al. | |
| 6,235,155 B1 | 5/2001 | Schroeder et al. | |
| 6,235,965 B1 | 5/2001 | Beihoffer et al. | |
| 6,261,580 B1 | 7/2001 | Lehrter et al. | |
| 6,270,893 B1 | 8/2001 | Young, Sr. et al. | |
| 6,274,667 B1 | 8/2001 | Shannon et al. | |
| 6,287,418 B1 | 9/2001 | Schroeder et al. | |
| 6,300,259 B1 | 10/2001 | Westland et al. | |
| 6,342,298 B1 | 1/2002 | Evans et al. | |
| 6,365,667 B1 | 4/2002 | Shannon et al. | |
| 6,376,072 B1 | 4/2002 | Evans et al. | |
| 6,379,498 B1 | 4/2002 | Burns et al. | |
| 6,392,116 B1 | 5/2002 | Beihoffer et al. | |
| 6,423,183 B1 | 7/2002 | Goulet et al. | |
| 6,432,268 B1 * | 8/2002 | Burghardt | 162/112 |
| 6,432,270 B1 | 8/2002 | Liu et al. | |
| 6,458,343 B1 | 10/2002 | Zeman et al. | |
| 6,461,553 B1 | 10/2002 | Hansen et al. | |
| 6,509,512 B1 | 1/2003 | Beihoffer et al. | |
| 6,511,580 B1 | 1/2003 | Liu | |
| 6,514,383 B1 | 2/2003 | Liu et al. | |
| 6,521,339 B1 | 2/2003 | Hansen et al. | |
| 6,552,245 B1 | 4/2003 | Roessler et al. | |
| 6,555,502 B1 | 4/2003 | Beihoffer et al. | |
| 6,582,560 B1 | 6/2003 | Runge et al. | |
| 6,599,393 B1 | 7/2003 | Liu | |
| 6,599,394 B1 | 7/2003 | Liu et al. | |
| 6,632,904 B1 | 10/2003 | Schroeder et al. | |
| 6,896,766 B1 | 5/2005 | Sarbo et al. | |
| 6,916,402 B1 | 7/2005 | Shannon et al. | |
| 6,936,136 B1 | 8/2005 | Shannon et al. | |
| 2001/0001312 A1 | 5/2001 | Mitchell et al. | |
| 2001/0007064 A1 | 7/2001 | Mitchell et al. | |
| 2001/0029358 A1 | 10/2001 | Beihoffer et al. | |
| 2001/0037100 A1 | 11/2001 | Shanklin | |
| 2001/0044612 A1 | 11/2001 | Beihoffer et al. | |
| 2002/0007166 A1 | 1/2002 | Mitchell et al. | |
| 2002/0015846 A1 | 2/2002 | Evans et al. | |
| 2002/0162243 A1 | 11/2002 | Runge et al. | |
| 2003/0014027 A1 | 1/2003 | Beihoffer et al. | |
| 2003/0124171 A1 | 7/2003 | Sun et al. | |
| 2003/0131962 A1 | 7/2003 | Lindsay et al. | |
| 2003/0208173 A1 | 11/2003 | Lagerstedt-Eidrup et al. | |
| 2004/0023579 A1 | 2/2004 | Kainth et al. | |
| 2004/0045687 A1 * | 3/2004 | Shannon et al. | 162/158 |
| 2004/0074622 A1 | 4/2004 | Liu et al. | |
| 2004/0084164 A1 | 5/2004 | Shannon et al. | |
| 2004/0084165 A1 | 5/2004 | Shannon et al. | |
| 2004/0086726 A1 | 5/2004 | Moline et al. | |
| 2004/0100376 A1 | 5/2004 | Lye et al. | |
| 2004/0118531 A1 | 6/2004 | Shannon et al. | |
| 2004/0163785 A1 | 8/2004 | Shannon et al. | |
| 2004/0234804 A1 | 11/2004 | Liu et al. | |
| 2004/0253890 A1 | 12/2004 | Ostgard et al. | |
| 2005/0136265 A1 | 6/2005 | Liu et al. | |
| 2005/0136759 A1 | 6/2005 | Shannon et al. | |
| 2005/0137547 A1 | 6/2005 | Garnier et al. | |

FOREIGN PATENT DOCUMENTS

| | | |
|---|---|---|
| EP | 0 192 216 B1 | 6/1990 |
| EP | 0 217 032 B1 | 2/1992 |
| WO | WO 98/19013 A1 | 5/1998 |
| WO | WO 99/25393 A2 | 5/1999 |
| WO | WO 99/25745 A1 | 5/1999 |
| WO | WO 99/25748 A1 | 5/1999 |
| WO | WO 00/56959 A1 | 9/2000 |
| WO | WO 00/63295 A1 | 10/2000 |
| WO | WO 01/49937 A1 | 7/2001 |
| WO | WO 02/10032 A2 | 2/2002 |
| WO | WO 02/34184 A1 | 5/2002 |
| WO | WO 02/072951 A2 | 9/2002 |
| WO | WO 2002/077048 A2 | 10/2002 |
| WO | WO 2002/081819 A1 | 10/2002 |
| WO | WO 03/018671 A1 | 3/2003 |
| WO | WO 03/037392 A1 | 5/2003 |
| WO | WO 2004/044327 A1 | 5/2004 |
| WO | WO 2004/050995 A1 | 6/2004 |
| WO | WO 2004/101684 A1 | 11/2004 |

OTHER PUBLICATIONS

TAPPI Official Test Method T 410 om-98, "Grammage of Paper and Paperboard (Weight Per Unit Area)," published by the TAPPI Press, Atlanta, Georgia, revised 1998, pp. 1-5.

TAPPI Official Test Method T 411 om-89, "Thickness (Caliper) of Paper, Paperboard, and Combined Board," published by the TAPPI Press, Atlanta, Georgia, revised 1989, pp. 1-3.

TAPPI Official Test Method T 530 pm-89, "Size Test for Paper By Ink Resistance (Hercules Method)," published by the TAPPI Press, Atlanta, Georgia, revised 1989, pp. 1-5.

Foulger, M. et al., "New Technology to Apply Starch and Other Additives," *Pulp & Paper Canada*, vol. 100, No. 2, 1999, pp. 24-25.

* cited by examiner

HYDROPHILIC FIBERS CONTAINING SUBSTANTIVE POLYSILOXANES AND TISSUE PRODUCTS MADE THEREFROM

BACKGROUND OF THE INVENTION

In the manufacture of tissue products, such as facial tissue, bath tissue, paper towels, dinner napkins and the like, a wide variety of product properties are imparted to the final product through the use of chemical additives. One common attribute imparted to tissue sheets through the use of chemical additives is softness. There are two types of softness that are typically imparted to tissue sheets through the use of chemical additives. The two types are bulk softness and topical or surface softness.

Bulk softness may be achieved by a chemical debonding agent. Such debonding agents are typically quaternary ammonium entities containing long chain alkyl groups. The cationic quaternary ammonium entity allows for the agent to be retained on the cellulose via ionic bonding to anionic groups on the cellulose fibers. The long chain alkyl groups provide softness to the tissue sheet by disrupting fiber-to-fiber hydrogen bonds within the tissue sheet.

Such disruption of fiber-to-fiber bonds provides a twofold purpose in increasing the softness of the tissue sheet. First, the reduction in hydrogen bonding produces a reduction in tensile strength thereby reducing the stiffness of the tissue sheet. Secondly, the debonded fibers provide a surface nap to the tissue sheet enhancing the "fuzziness" of the tissue sheet. This tissue sheet fuzziness may also be created through use of creping as well, where sufficient interfiber bonds are broken at the outer tissue surface to provide a plethora of free fiber ends on the tissue surface.

A multi-layered tissue structure may be utilized to enhance the softness of the tissue sheet. In this embodiment, a thin layer of strong softwood fibers is used in the center layer to provide the necessary tensile strength for the tissue product. The outer layers of such structures may be composed of the shorter hardwood fibers, which may or may not contain a chemical debonder.

The topical or surface softness of a tissue sheet, and ultimately the resulting tissue product, may be achieved by topically applying an emollient to the surface of the tissue sheet or tissue product. The word emollient is used here in the sense that it makes the tissue sheet less harsh or abrasive. One such emollient is polysiloxane. Polysiloxane treated tissues are described in U.S. Pat. No. 4,950,545, issued on Aug. 21, 1990 to Walter et al.; U.S. Pat. No. 5,227,242, issued on Jul. 13,1993 to Walter et al.; U.S. Pat. No. 5,558,873, issued on Sep. 24, 1996 to Funk et al.; U.S. Pat. No. 6,054,020, issued on Apr. 25, 2000 to Goulet et al.; U.S. Pat. No. 6,231,719, issued on May 15, 2001 to Garvey et al.; and, U.S. Pat. No. 6,432,270, issued on Aug. 13, 2002 to Liu et al., which are incorporated by reference to the extent that they are non-contradictory herewith. A variety of substituted and non-substituted polysiloxanes may be used.

While polysiloxanes may provide improved softness in a tissue sheet and/or tissue product, there may be some drawbacks to their use. First, polysiloxanes are generally hydrophobic, that is, they tend to repel water. Tissue sheets and/or tissue products treated with polysiloxane tend to be less absorbent than tissue sheets and/or tissue products not containing polysiloxanes. For many applications, particularly sanitary bath tissue, this significantly reduces the utility of polysiloxanes to create softness in the tissue sheet and/or tissue product. Hydrophilic polysiloxanes are known in the art, however, such hydrophilic polysiloxanes are typically more water soluble and hence when applied to a tissue sheet and/or tissue product will tend to migrate more in the z-direction of the tissue sheet and/or tissue product than the hydrophobic polysiloxanes. Hydrophilic polysiloxanes typically are also usually sold at a cost premium to the hydrophobic polysiloxanes. The hydrophobic portion of the polysiloxane, referred to as the polydialkylpolysiloxane portion, also tends to have a more significant impact on improving softness. Hence, hydrophilic polysiloxanes also tend to be less effective at softening and more costly to use than hydrophobic polysiloxanes.

An additional disadvantage to the use of polysiloxanes is the effect of aging on hydrophobicity. Elevated temperatures and time may significantly increase the hydrophobicity of treated tissue sheets and/or tissue products and, in cases such as bath tissue, may render the bath tissue product unacceptable for a given application after a certain period of time or under certain environmental conditions.

Polysiloxanes tend to be poorly retained if applied to a slurry of pulp fibers in the wet end of the tissue process. Unretained polysiloxane as well as the additional surfactants required to make emulsions suitable for wet end application can cause significant issues in the tissue making process, rendering wet end application of polysiloxanes infeasible. Furthermore, if applied in the wet end of the tissue making process, hydrophilic polysiloxanes are even more poorly retained on the pulp fibers than the hydrophobic polysiloxanes due to the enhanced water solubility.

For water insoluble polysiloxanes, poor retention of the polysiloxane in the wet end of the tissue machine may be circumvented by treating the pulp fibers at the pulp mill with the polysiloxane prior to final drying of the tissue sheet. Such a process is described in U.S. Pat. No. 6,582,560, issued on Jun. 24, 2003 to Runge, et. al. and which is incorporated by reference to the extent that it is non-contradictory herewith. When used in tissue sheet and/or tissue product, the polysiloxane pretreated pulp fibers may significantly enhance the softness of the tissue sheet and/or tissue product.

Unfortunately, use of these polysiloxane pretreated pulp fibers in tissue sheets or tissue products may lead to unacceptably high levels of hydrophobicity even when low levels of polysiloxane are used. In certain cases, the degree of hydrophobicity introduced into the tissue sheet using polysiloxane pretreated pulp fibers is greater than when the same level of polysiloxane is topically applied to the tissue sheet by the methods known in the art. Additionally, increases in hydrophobicity brought on by heat aging are also present in both the polysiloxane pretreated pulp fibers and/or tissue products made from the polysiloxane pretreated pulp fibers.

Co-pending U.S. patent application Ser. No. 10/289557 filed on Nov. 6, 2002, describes a method to reduce the hydrophobicity associated with use of pulp fibers pretreated with hydrophobic polysiloxanes by altering the layer structure of the tissue sheet. More specifically, by concentrating the polysiloxane fibers towards the exterior surface of the tissue sheet, the hydrophobicity limitations of using pulp fibers pretreated with hydrophobic polysiloxanes in absorbent tissue sheets is overcome. While this method provides a significant improvement in reducing the hydrophobicity of the tissue sheet it does limit use to layered tissue sheets and also generally reduces the amount of total polysiloxane that may be applied. Additionally, while the hydrophobicity is greatly improved, wet out times may still be unacceptably high for bath tissue and similar tissue products.

Co-pending U.S. patent application Ser. No. 10/325484, filed on Dec. 19, 2002, describes a method for applying surfactants topically to the base tissue web to mitigate the hydrophobicity of tissue sheets including tissue sheets prepared with pulp fibers pretreated with hydrophobic polysiloxanes. While this method again improves the hydrophobicity of such tissue sheets, it does require topical application of a surfactant to the tissue sheet and, hence, requires additional capital and added complexity in the tissue making process. An additional disadvantage to using external surfactants is that at least a portion of the surfactants are lost in broke repulping operations. Thus, while the virgin tissue product may be hydrophilic, incorporation of this material into a broke stream could result in tissue products having unacceptable hydrophobicity.

Therefore, there is a need for polysiloxane pretreated pulp fibers that have improved hydrophilic properties while still providing for softness enhancement in tissue sheets and tissue products where the polysiloxane pretreated pulp fibers are incorporated. There is a further need to have the polysiloxane be well retained through the wet end of the paper or tissue making process. There is a further need to be able to utilize such polysiloxane pretreated pulp fibers without the addition of surfactants or other agents to improve the hydrophilicity of the tissue sheets or tissue products made from the polysiloxane pretreated pulp fibers. There is a further need to have the polysiloxane pretreated pulp fibers retain their hydrophilicity when recycled or used in broke and to have the polysiloxane pretreated pulp fibers and tissue sheets or tissue products containing the polysiloxane pretreated pulp fibers exhibit good thermal and aging stability with regard to hydrophobicity.

There is an interest to create polysiloxane pretreated pulp fibers having good retention of polysiloxane through the wet end of the paper making process, provide enhanced softness to products containing the fibers and yet demonstrate improved hydrophilic properties relative to use of hydrophobic polysiloxanes alone. It has now been discovered that pulp fibers pretreated with certain amino functional polyether polysiloxanes may be retained very well through the wet end of the papermaking process despite having excellent hydrophilic properties. Furthermore, such polysiloxane pretreated pulp fibers are effective at improving softness of tissue sheets or tissue products containing the polysiloxane pretreated pulp fibers and providing for enhanced thermal stability relative to hydrophobicity generation. It has also been further discovered that these polysiloxanes may be used in conjunction with hydrophobic polysiloxanes to significantly improve the hydrophilic nature of the pulp fibers and associated tissue sheets or tissue products containing the polysiloxane pretreated pulp fibers.

SUMMARY OF THE INVENTION

While the pulp fibers of the present invention may be useful to a variety of products, particular interest may be in tissue and towel products. It is understood that the term "tissue sheet" as used herein refers to tissue and towel sheets. The term "tissue product" as used herein refers to tissue and towel products. Tissue and towel products as used herein are differentiated from other paper products in terms of their bulk. The bulk of the tissue and towel products of the present invention is calculated as the quotient of the caliper (hereinafter defined), expressed in microns, divided by the basis weight, expressed in grams per square meter. The resulting bulk is expressed as cubic centimeters per gram. Writing papers, newsprint and other such papers have higher strength, stiffness and density (low bulk) in comparison to tissue and towel products which tend to have much higher calipers for a given basis weight. The tissue and towel products of the present invention may have a bulk of about 2 $cm^3/g$ or greater, more specifically about 2.5 $cm^3/g$ or greater, and still more specifically about 3 $cm^3/g$ or greater.

The term "layered tissue sheet" as used herein refers to the formation of a stratified tissue sheet, wherein a particular tissue sheet or tissue sheets making up a multi-ply tissue product contain a z-directional fiber gradient. In one method of the formation of a layered tissue sheet, individual slurries of pulp fibers are sent to a divided headbox and applied to a moving belt where the pulp fibers are dewatered by any of a variety of processes and further dried to form a tissue sheet that has a specific distribution of fibers in the z-direction based on the split of the individual furnishes. Two or more layers may be present in a given tissue sheet of a multi-ply tissue product. The term "blended sheet" as used herein refers to the formation of a single layered or layered sheet where there is a homogeneous distribution of fibers in the z-direction of the sheet. Blended tissue sheets may also be referred to as non-layered or unlayered tissue sheets. The term "non-treated pulp fibers" as used herein refers to pulp fibers that have not been pretreated with a polysiloxane of the present invention. It is understood that the pulp fibers may be treated with other chemical additives used in tissue making processes.

The term "substantively affixing" as used herein refers to the ability of a group on the polysiloxane molecule to bind the polysiloxane molecule to the substrate pulp fibers in such a manner that the polysiloxane molecule is highly retained on the pulp fibers through all subsequent processing steps that the pulp fibers go through to make the final product.

The particular structure of the polysiloxanes of the present invention may provide the desired product properties to the pulp fibers and tissue sheets and/or tissue products made therewith. Polysiloxanes encompass a very broad class of compounds. They are characterized in having a backbone structure:

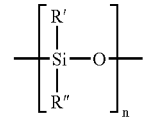

where R' and R" may be a broad range of organo and non-organo groups including mixtures of such groups and where n is an integer $\geq 2$. These polysiloxanes may be linear, branched, or cyclic. They may include a wide variety of polysiloxane copolymers containing various compositions of functional groups, hence, R' and R" actually may represent many different types of groups within the same polymer molecule. The organo or non-organo groups may be capable of reacting with pulp fibers to covalently, ionically or hydrogen bond the polysiloxane to the pulp fibers. These functional groups may also be capable of reacting with themselves to form crosslinked matrixes with the pulp fibers. The scope of the present invention should not be construed as limited by a particular polysiloxane structure so long as that polysiloxane structure delivers the aforementioned product benefits to the pulp fibers, tissue sheets and/or the final tissue products. One aspect of the polysiloxanes of the present invention is the ability to substantively affix themselves to pulp fibers such that they are retained in the wet end of the paper making process.

While not wishing to be bound by theory, the softness benefits that polysiloxanes deliver to pulp fibers pretreated with the polysiloxanes of the present invention may be, in part, related to the molecular weight of the polysiloxane. Viscosity is often used as an indication of molecular weight of the polysiloxane as exact number average or weight average molecular weights may be difficult to determine. The viscosity of the polysiloxanes of the present invention may be about 25 centipoise or greater, more specifically about 50 centipoise or greater, and most specifically about 100 centipoise or greater. The term "viscosity" as referred to herein refers to the viscosity of the neat polysiloxane itself and not to the viscosity of an emulsion if so delivered. It should also be understood that the polysiloxanes of the present invention may be delivered as solutions containing diluents. Such diluents may lower the viscosity of the polysiloxane solution below the limitations set above, however, the efficacious part of the polysiloxane should conform to the viscosity ranges given above. Examples of such diluents include but is not limited to oligomeric and cyclo-oligomeric polysiloxanes such as octamethylcyclotetrasiloxane, octamethyltrisiloxane, decamethylcyclopentasiloxane, decamethyltetrasiloxane and the like, including mixtures of these diluents.

The particular form in which the polysiloxanes of the present invention are delivered to the pulp fibers in the manufacture of the polysiloxane pretreated pulp fiber may be any form known in the art. Polysiloxanes useful for the present invention may be delivered as neat fluids; aqueous or non-aqueous solutions; aqueous or non-aqueous dispersions; and, emulsions, including microemulsions, stabilized by suitable surfactant systems that may confer a charge to the emulsion micelles. Nonionic, cationic, and anionic systems may be employed. To maximize retention of the polysiloxane during the manufacturing process of the tissue sheet and/or tissue product, it may be desirable to add the polysiloxane to the pulp fiber as a neat fluid. The amount of polysiloxane retained during the process of making a wet laid tissue sheet may be measured by the silicone retention factor. The silicone retention factor is determined by measuring the level of polysiloxane in the polysiloxane pretreated pulp fibers ($Si^f$), forming a tissue sheet and/or tissue product (typically a tissue handsheet) incorporating the polysiloxane pulp fibers and measuring the amount of the polysiloxane present in the tissue sheet and/or tissue product (tissue handsheet) ($Si^h$). The silicone retention factor is then calculated using the following equation:

Silicone Retention Factor=$(Si^h)/(Si^f)$

The silicone retention factor of the present invention may range from about 0.6 or greater, about 0.7 or greater, or about 0.8 or greater.

The non-treated pulp fibers used in the present invention may or may not be the same type of pulp fibers that are treated with a polysiloxane of the present invention. The polysiloxane pretreated pulp fibers of the present invention may comprise any pulp fiber type or combinations thereof, including but not limited to hardwood pulp fibers, softwood pulp fibers, or combinations thereof. The layers comprising non-treated pulp fibers may be composed of any pulp fiber type or combinations thereof, the same or different from the outer layers containing the silicone pretreated pulp, including but not limited to hardwood pulp fibers, softwood pulp fibers, or combinations thereof. It is understood that the pulp fibers comprising the non-treated pulp fibers of the present invention may or may not be the same as the polysiloxane pretreated pulp fibers or combinations thereof of the present invention.

In another embodiment, the invention may reside in a method for making a soft, economical, absorbent tissue product comprising hydrophilic polysiloxane pretreated pulp fibers. The method may comprise: (a) forming a first aqueous suspension of pulp fibers comprising polysiloxane pretreated pulp fibers; (b) optionally forming at least a second aqueous suspension of pulp fibers comprising non-treated pulp fibers; (c) forwarding the first aqueous suspension of pulp fibers comprising polysiloxane pretreated pulp fibers to a single layer headbox or a stratified headbox; (d) forwarding the optional second aqueous suspension of pulp fibers comprising non-treated pulp fibers to the stratified headbox such that the second suspension of pulp fibers is directed to an inner layer; (e) depositing the first and optional second aqueous suspensions of pulp fibers onto a forming fabric to form a wet layered tissue sheet; (f) dewatering the tissue sheet to form a dewatered layered tissue sheet; and, (g) drying the dewatered tissue sheet to form a dried layered tissue sheet. The dried layered tissue sheet may be converted into a tissue product. If using a stratified headbox, the polysiloxane pretreated pulp fibers are preferably directed to at least one outer layer of the dried tissue sheet.

THE DETAILED DESCRIPTION OF THE INVENTION

Figure 1:
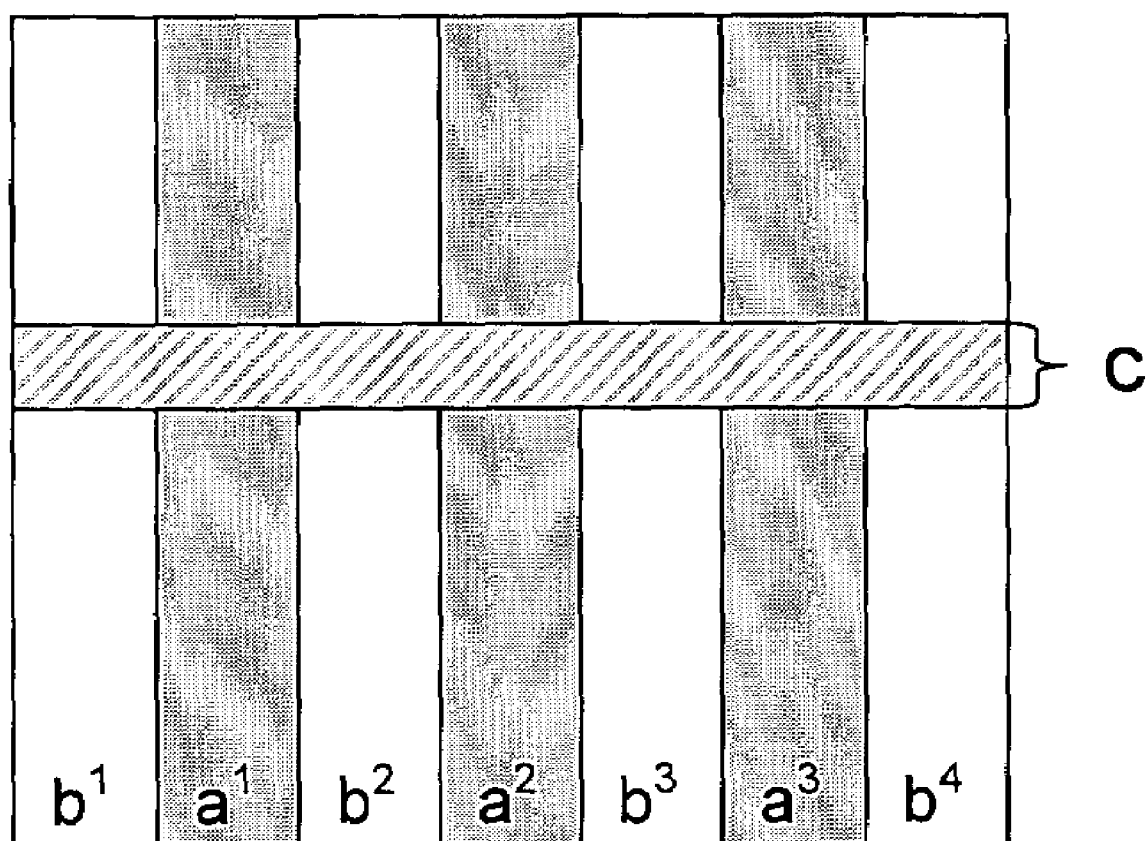
FIG. 1 represents a plan view of a tissue product comprising the present invention.

In the present invention, a high level of polysiloxane is retained on the polysiloxane pretreated pulp fibers through the tissue making process despite the polysiloxane having a high level of hydrophilicity. The amount of the polysiloxane retained during processing needed to make a wet laid tissue sheet and/or tissue product may be measured by the silicone retention factor. The silicone retention factor is determined by measuring the level of polysiloxane in the polysiloxane pretreated pulp fibers ($Si^f$), forming a tissue sheet and/or tissue product (typically a tissue handsheet) incorporating the polysiloxane pulp fibers and measuring the amount of the polysiloxane present in the tissue sheet and/or tissue product (tissue handsheet) ($Si^h$). The silicone retention factor is then calculated using the following equation:

Silicone Retention Factor=$(Si^h)/(Si^f)$

The silicone retention factor may range from about 0.6 or greater, about 0.7 or greater, or about 0.8 or greater. While not wishing to be bound by theory, the retention of the polysiloxanes in the present invention may be due at least in part to the presence of a functional groups on the hydrophilic polysiloxane capable of substantively affixing the hydrophilic polysiloxane to the pulp fibers. An exemplary group is an amino functional group. These amino groups may be capable of bonding with pulp fibers in a manner that enables the polysiloxanes to be retained through the wet end of the tissue making process.

The polysiloxane pretreated pulp fibers of the present invention are found to have excellent hydrophilic properties. The hydrophilicity of the polysiloxane pretreated pulp fibers may be measured using the water drop test described herein after. The water drop test measures the amount of time it takes a handsheet prepared from the polysiloxane pretreated pulp fibers to absorb a given amount of water. The polysiloxane pretreated pulp fibers retain their hydrophilic properties upon thermal aging as measured by the aged water drop test. In one embodiment of the present invention, the polysiloxane pretreated pulp fibers have a water drop test time after aging at about 85° C. for one hour of about 180 seconds or less. In another embodiment of the present invention, the polysiloxane pretreated pulp fibers have a water drop test time after aging at about 85° C. for one hour of about 120 seconds or less. In another embodiment of the present invention, the polysiloxane pretreated pulp fibers have a water drop test time after aging at about 85° C. for one hour of about 60 seconds or less. In still another embodiment of the present invention, the polysiloxane pretreated pulp fibers have a water drop test time after aging at about 85° C. for one hour of about 30 seconds or less.

While not wishing to be bound by theory, the softness benefits that polysiloxanes deliver to pulp fiber containing products is believed to be, in part, related to the molecular weight of the polysiloxane. Viscosity is often used as an indication of molecular weight of the polysiloxane as exact number or weight average molecular weights are often difficult to determine. The viscosity of the polysiloxanes of the present invention is about 25 centipoise or greater, more specifically about 50 centipoise or greater, and most specifically about 100 centipoise or greater. The term "viscosity" as referred to herein refers to the viscosity of the neat polysiloxane itself and not to the viscosity of an emulsion if so delivered. It should also be understood that the polysiloxanes of the present invention may be delivered as solutions containing diluents. Such diluents may lower the viscosity of the solution below the limitations set above, however, the efficacious part of the polysiloxane should conform to the viscosity ranges given above. Examples of such diluents may include, but is not limited to: oligomeric and cyclo-oligomeric polysiloxanes such as octamethylcyclotetrasiloxane, octamethyltrisiloxane, decamethylcyclopentasiloxane, decamethyltetrasiloxane and the like, including mixtures of these compounds.

The level of total polysiloxane in the polysiloxane pretreated pulp fibers may be determined by any method known in the art. If the particular polysiloxane applied to the polysiloxane pretreated pulp fibers is known, the total amount of polysiloxane may be measured by converting the dialkylpolysiloxane component of the polysiloxane to the corresponding dialkyldiflouro silane using $BF_3$ followed by GC quantification of the dialkylpolysiloxane as described herein.

When the specific polysiloxane applied to the polysiloxane pretreated pulp fibers is not known, X-ray Fluorescence Spectroscopy (XRF) may also be used. An example of a suitable instrument is the Lab-X3500 X-ray Fluorescence Analyzer (XRF) available from Oxford Instruments Analytical, LTD, Elk Grove Village, Ill. When using XRF spectroscopy it is not necessary to know the exact concentration of polysiloxane in the sample. X-ray counts between the treated pulp fibers and the handsheets are compared and retention factor determined from the ratio of counts in the handsheet to counts in the pulp fibers.

When the silicone is applied in a non-uniform manner to the tissue sheet and/or tissue product, it is necessary to take the test specimen in a manner so as to replicate the repeat pattern in the tissue sheet and/or tissue product so the sample of the tissue sheet and/or tissue product has the same % area coverage as the rest of the tissue sheet and/or tissue product. For example, referring to. FIG. 1, the shaded areas $a^1$, $a^2$, $a^3$ represent silicone treated areas on the tissue sheet and/or tissue product (p) while areas $b^1$ through $b^4$ represent untreated areas of the tissue sheet and/or tissue product. In FIG. 1, the silicone is applied in stripes in the machine direction. In this case the test sample strip (C) is taken in the cross direction so that the sample of the tissue sheet and/or tissue product to be tested has the same ratio of treated to untreated regions as the entire tissue sheet and/or tissue product and hence same proportion of polysiloxane to the polysiloxane pretreated pulp fibers as the tissue sheet and/or tissue product (p).

As an alternative, the tissue sheet and/or tissue product or a portion thereof may be dry fiberized to obtain a homogeneous distribution of silicone in the sample to be tested. Dry fiberization is a dry mechanical treatment in which shredded pulp fiber lap is passed through a device, such as a hammermill, similar to a refiner; the resultant material is fluff pulp fiber. Specific equipment and conditions are not important so long as parameters such as anvil gap and feed throughput are controlled so as to achieve good uniformity. This method may be required when using XRF spectroscopy to determine the amount of polysiloxane present in the tissue sheet and/or tissue product.

Uniformity of the polysiloxane in the x-y direction of the pulp fiber sheet may be determined using Micro-XRF imaging techniques. One suitable instrument for determining the X-Y silicone distribution is the Omnicron EDXRF system available from ThermoNoran, Inc., located in Madison, Wis. If the uniformity of the polysiloxane distribution in the pulp fiber sheet can not be ascertained via the Micro-XRF imaging technique, another acceptable alternative is to pulp the entire pulp fiber sheet for 5 minutes at 2.5% consistency after soaking for 5 minutes. Approximately 2-liters of the pulp fiber slurry should then be taken and used to prepare tissue handsheets as described hereinafter.

Another surprising element of the present invention is the ability of the pulp fibers to retain their hydrophilicity even when used in conjunction with hydrophobic polysiloxanes such as amino functional polydialkylsiloxanes. Higher levels of polydialkylsiloxanes allow for improved softness in tissue sheets and/or tissue products made with the polysiloxane pretreated pulp fibers. In one embodiment of the present invention, the amount of polydialkylsiloxane present in the polysiloxane pretreated pulp fibers may be about 0.2% or greater by weight of the total fiber weight. In another embodiment of the present invention, the amount of polydialkylsiloxane present in the polysiloxane pretreated pulp fibers may be about 0.5% or higher by weight of the total fiber weight. In another embodiment of the present invention, the amount of polydialkylsiloxane present in the polysiloxane pretreated pulp fibers may be about 0.8% or greater by weight of the total fiber weight. In still another embodiment of the present invention, the amount of polydialkylsiloxane present in the polysiloxane pretreated pulp fibers may be about 1% or greater by weight of the total fiber weight. In still another embodiment of the present invention, the amount of polydialkylsiloxane present in the polysiloxane pretreated pulp fibers may be from about 0.3% to about 10% by weight of the total fiber weight.

Many cellulosic pulp fiber types may be used for the polysiloxane pretreated fibers of the present invention including hardwood or softwoods, straw, flax, milkweed seed floss fibers, abaca, hemp, kenaf, bagasse, cotton, reed, and the like. All known cellulosic papermaking pulp fibers may be used, including bleached and unbleached fibers, fibers of natural origin (including wood fiber, cotton fiber and other cellulose fibers, cellulose derivatives, and chemically stiffened or crosslinked fibers), synthetic cellulosic fibers (rayon, lyocell), virgin and recovered or recycled fibers, hardwood and softwood, and fibers that have been mechanically pulped (e.g., groundwood), chemically pulped (including but not limited to the kraft and sulfite pulp processings), thermomechanically pulped, chemithermomechanically pulped, and the like. Mixtures of any subset of the above mentioned or related fiber classes may be used. The pulp fibers may be prepared in a multiplicity of ways known to be advantageous in the art. Useful methods of preparing fibers include dispersion to impart curl and improved drying properties, such as disclosed in U.S. Pat. No. 5,348,620, issued on Sep. 20, 1994 and U.S. Pat. No. 5,501,768 issued Mar. 26, 1996, both issued to M. A. Hermans et al. and U.S. Pat. No. 5,656,132, issued on Aug. 12, 1997 to Farrington, Jr. et al.

The particular form in which the polysiloxanes of the present invention are delivered to the pulp fibers in the manufacture of the polysiloxane pretreated pulp fiber may be any form known in the art. Polysiloxanes useful for the present invention may be delivered as neat fluids; aqueous or non-aqueous solutions; aqueous or non-aqueous dispersions; and, emulsions, including microemulsions, stabilized by suitable surfactant systems that may confer a charge to the emulsion micelles. Nonionic, cationic, and anionic systems may be employed. To maximize retention of the polysiloxane during the manufacturing process of the tissue sheet and/or tissue product, it may be desirable to add the polysiloxane to the pulp fiber as a neat fluid. In one embodiment of the present invention, the pulp fibers may be pretreated as described in U.S. Pat. No. 6,582,560 issued to Runge, et. al., on Jun. 24, 2003.

Polysiloxane surfactants and wetting agents may be used in conjunction with polysiloxanes to reduce the hydrophobicity of articles treated with hydrophobic polysiloxanes. These polysiloxane surfactants and wetting agents are low molecular weight, low viscosity materials having very high levels of ethylene oxide side chains and very few, if any, polydialkylsiloxane units. The low viscosity, high level of substitution and low level of polydialkylsiloxane units prevents these polysiloxane surfactants from providing a noticeable softness benefit to tissue sheets and/or tissue products treated with these polysiloxanes or containing polysiloxane pretreated pulp fibers. Furthermore, they do not have groups capable of anchoring themselves to pulp fibers and hence are not retained in the wet end of the tissue making process. Loss of the surfactant polysiloxane may cause the polysiloxane pretreated pulp fibers to form hydrophobic tissue sheets and/or tissue products. While not wishing to be bound by theory, it is believed that the hydrophilic polysiloxanes of the present invention provide both wetting and softness improvement due to their high molecular weight, presence of polydialkylsiloxane units on the polysiloxane molecule and presence of amino groups or other group on the silicone molecule capable of substantively affixing the polysiloxane to the pulp fibers such that the hydrophilic polysiloxane is retained in the tissue sheet and/or tissue product.

The polysiloxane pretreated pulp fibers of the present invention may be used in a variety of applications, including, but not limited to tissue, towels, wipers, wet wipes, and other personal care products utilizing pulp fibers. Any process may be used to make such tissue sheets and/or tissue products including but not limited to wet-laid, air-laid, hydroentangling and the like. As stated above, the pretreated fibers are particularly well suited to preparation of wet laid tissue sheets, such sheets include tissue and towel sheet and the resulting tissue and towel products. Tissue sheets and/or tissue products as used herein are differentiated from other tissue products in terms of its bulk. The bulk of the tissue sheets and/or tissue products of the present invention may be calculated as the quotient of the caliper (hereinafter defined), expressed in microns, divided by the basis weight, expressed in grams per square meter. The resulting bulk is expressed as cubic centimeters per gram. Writing papers, newsprint and other such papers have higher strength, stiffness and density (low bulk) in comparison to tissue products of the present invention which tend to have much higher calipers for a given basis weight. The tissue sheets and/or tissue products of the present invention have a bulk of about 2 $cm^3/g$ or greater, more specifically about 2.5 $cm^3/g$ or greater, and still more specifically about 3 $cm^3/g$ or greater.

The basis weight and caliper of the multi-ply tissue products of the present invention may vary widely and may be dependent on, among other things, the number of plies (tissue sheets). The caliper and bulk of the plies comprising non-treated pulp fibers may be of any value. The caliper of the individual ply or plies comprising the polysiloxane pretreated pulp fibers may be about 1200 microns or less, more specifically about 1000 microns or less, and still more specifically about 800 microns or less. The bulk of the individual ply or plies comprising the polysiloxane pretreated pulp fibers may be about 2 $g/cm^3$ or greater, more specifically about 2.5 $g/cm^3$ or greater, and most specifically about 3 $g/cm^3$ or greater.

Pulp fibers not pretreated with polysiloxane may be blended with pulp fibers pretreated with polysiloxane in the layer or layers comprising the polysiloxane pretreated pulp fibers. The ratio of polysiloxane pretreated pulp fibers to non-treated pulp fibers in any layer of the tissue sheet comprising the polysiloxane pretreated pulp fibers may vary widely and may range from about 5% to about 100% by weight on a dry fiber basis, more specifically from about 10% to about 100% by weight on a dry fiber basis, and still most preferably from about 10% to about 90% by weight on a dry fiber basis. The total weight of polysiloxane pretreated pulp fibers relative to the total weight of the pulp fibers (both polysiloxane pretreated pulp fibers and non-treated pulp fibers) in the tissue sheet comprising the polysiloxane pretreated pulp fibers may vary widely from about 0.5% to about 100% on a dry pulp fiber basis, more specifically from about 5% to about 90% on a dry pulp fiber basis, and most specifically from about 10% to about 80% on a dry pulp fiber basis.

The total amount of polysiloxane in the tissue sheet may vary widely but may range from about 0.01% to about 5% by weight of the total dry pulp fiber weight of the tissue sheet, more specifically from about 0.02% to about 3% by weight of the total dry pulp fiber weight of the tissue sheet, and most preferably from about 0.03% to about 2% by weight of the total dry pulp fiber weight of the tissue sheet.

In a specific embodiment of the present invention, the tissue product is a single or multi-ply tissue product comprising non-layered (blended) tissue sheets containing the polysiloxane pretreated pulp fibers. In another embodiment of the present invention, the tissue product is a multi-ply tissue product having two outer surfaces wherein both outer tissue sheets of the multi-ply product are layered tissue sheets comprising polysiloxane pretreated pulp fibers. The outer surfaces of the tissue product are comprised of layers comprising polysiloxane pretreated pulp fibers. In another specific embodiment of the present invention, the tissue product is a single ply tissue product comprising at least a 3-layer tissue sheet wherein both outer layers comprise pretreated polysiloxane pulp fibers and at least one inner layer comprises non-treated pulp fibers.

Figure 2:
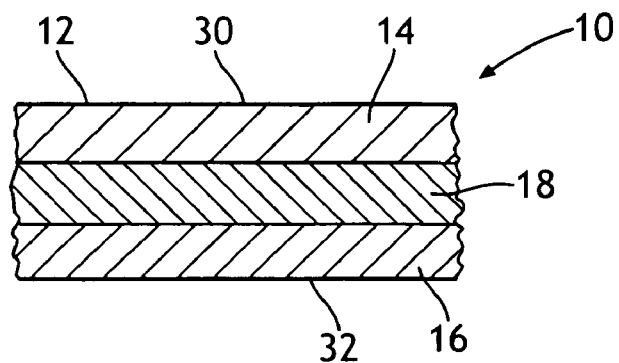
FIG. 2 is a diagram of a tissue sheet of the present invention having three layers.
Figure 3:
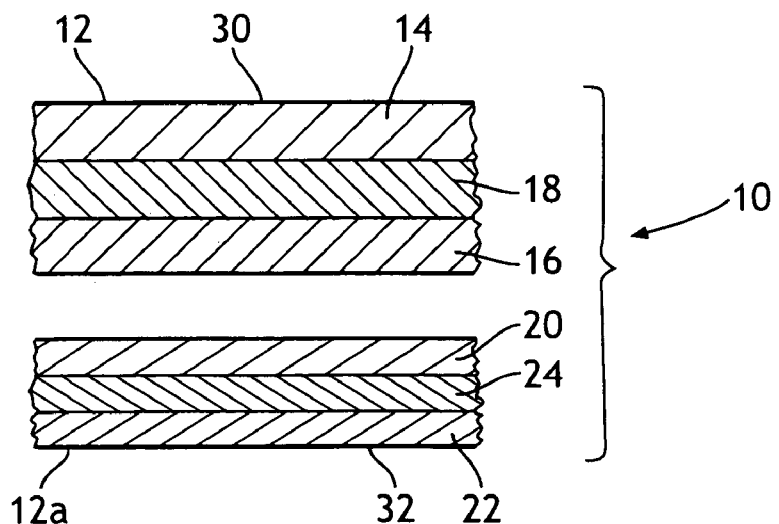
FIG. 3 is a diagram of two tissue sheets of the present invention, each tissue sheet having three layers.

One embodiment of the present invention may employ a three-layer structure. FIG. 2 shows a tissue sheet 12 consisting of a three layers 14, 16, and 18. FIG. 3 shows two outer tissue sheets 12 and 12a of a multi-ply tissue product 10, the outer tissue sheets 12 and 12a comprise three-layer structures. The layer or layers of the tissue sheets 12 and/or 12a containing the polysiloxane pretreated pulp fibers are adjacent to a layer not containing polysiloxane pretreated pulp fibers. The relative width of the layer or layers containing the polysiloxane pretreated pulp fibers to the width of the adjacent layer containing non-treated pulp fibers may be calculated from weight % of the pulp fiber in the layers comprising the polysiloxane pretreated pulp fibers and the weight % of non-treated pulp fibers in the adjacent layer not containing the polysiloxane pretreated pulp fibers. The weight ratios, also known as fiber splits are used to express the width of the individual layers.

Figure 4:
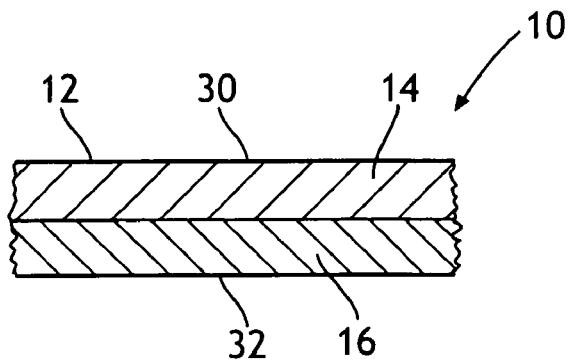
FIG. 4 is a diagram of a tissue sheet of the present invention having two layers.

Single or multiply tissue products 10 may be made from layered tissue sheets 12. Referring to FIG. 2, in a single ply layered tissue product 10, the polysiloxane pretreated pulp fibers may lie in the first outer layer 14 or the second layer outer 16 or both the first and second outer layers 14 and 16 of the tissue sheet 12 of the tissue product 10. In one embodiment of a single ply tissue product 10, the polysiloxane pretreated pulp fibers are positioned in the first and second outer layers 14 and 16 while the inner layer 18 comprises pulp fibers not pretreated with polysiloxane. In another embodiment of a single ply tissue product 10, the polysiloxane pretreated pulp fibers are positioned in one of the first and second outer layers 14 and 16 while the inner layer 18 comprises pulp fibers not pretreated with polysiloxane and the other outer layer 16 or 14 comprises non-treated pulp fibers. In another embodiment of the present invention, as shown in FIG. 4, in a two layer single-ply tissue product 10, the polysiloxane pretreated pulp fibers are positioned in only one of the first and second outer layers 14 or 16 while the other outer layer 16 or 14 would comprise non-treated pulp fibers. In such a two layered embodiment, the inner layer 18 is understood not to be present in the two layered single tissue sheet 12.

Referring to FIG. 3, in multi-ply tissue products 10, the polysiloxane pretreated pulp fibers may be positioned in at least one of the outer first layers 14 and 22 of the tissue sheets 12 and 12a which form the outer surfaces 30 and 32, respectively, of a multi-ply-tissue product 10. In another embodiment of the present invention, the polysiloxane pretreated pulp fibers may be positioned in the first outer layers 14 and 22 of the tissue sheets 12 and 12a, respectively, which form the outer surfaces 30 and 32 of the multi-ply tissue product 10. It should also be recognized that FIG. 3 represents only the outer tissue sheets 12 and 12a of the multi-ply tissue product 10. Any number of additional tissue sheets 12 may be contained between the two outer sheets 12 and 12a. Additional tissue sheets 12 may or may not contain polysiloxane pretreated pulp fibers. The tissue sheets 12 comprising non-treated pulp fibers may be layered or non-layered.

In some embodiments of the present invention, it is understood that the discussion of first outer layers 14 and 22 may also be applied to the second outer layers 16 and 20 as shown in FIG. 3. Additionally, in some embodiments of the present invention, the discussion of the first outer layers 14 and 22, the second outer layers 16 and 20, and the inner layers 18 and 24 may be applied to additional tissue sheets 12 that may be incorporated into multi-ply tissue products 10.

It is understood that tissue sheet 12 may or may not be the same as tissue sheet 12a, but the designation of 12 and 12a is provided to more clearly differentiate between the various tissue sheets 12 within the multi-ply tissue products 10 the present invention. It is also understood that the tissue sheets 12 (and tissue sheets 12 and 12a) of the present invention may or may not be the same as in that the tissue sheets 12 (or tissue sheets 12 and 12a) may comprise different pulp types and/or different percents of pulp types and of polysiloxane pretreated pulp fibers to non-treated pulp fibers.

In another embodiment of the present invention, a multi-ply tissue product 10 may have the polysiloxane pretreated pulp fibers positioned in first outer layers 14 and 22 of the two outer tissue sheets 12 and 12a while at least one of the inner layer or layers 16, 18, 20, and 24 of the tissue sheets 12 and 12a are comprised of pulp fibers not pretreated with polysiloxane. In another embodiment of the present invention, a multi-ply tissue product 10 may have the polysiloxane pretreated pulp fibers positioned in first outer layers 14 and 22 and in the second outer layers 16 and 20 of the two outer tissue sheets 12 and 12a while the inner layer or layers 18 and 24 of the tissue sheets 12 and 12a may be comprised of non-treated pulp fibers.

In some embodiments of the present invention, it is desirable in the tissue product 10 to position the outer layer or layers (for example, outer layers 14 and/or 22 as shown in FIG. 3 or outer layers 14 and/or 16 as shown in FIG. 2) comprising polysiloxane pretreated pulp fibers of the tissue sheets 12 and/or 12a such that the outer layer-or layers 14 and/or 22 (or alternatively, outer layers 14 and/or 16) comprising the polysiloxane pretreated pulp fibers are adjacent to an inner layer (for example, inner layers 18 and/or 24 as shown in FIG. 3 or inner layer 18 as shown in FIG. 2) comprising non-treated pulp fibers. In another embodiment of the present invention, one of the first and second outer layers 14 and 16 of the layered single ply tissue product 10 may comprise polysiloxane pretreated pulp fibers while the other outer layer 16 or 14 comprises non-treated pulp fibers and is adjacent the outer layer 14 or 16 comprising the polysiloxane pretreated pulp fibers.

The absorbency of the tissue product 10 and/or tissue sheet 12 may be determined by the Wet Out Time. As used herein, the term "Wet Out Time" is related to absorbency and is the time it takes for a given sample of a tissue sheet 12 to completely wet out when placed in water. The Wet Out Time (hereinafter defined) for tissue sheets 12 of the present invention may be about 180 seconds or less, more specifically about 120 seconds or less, still more specifically about 60 seconds or less, and still more specifically about 30 seconds or less.

In a multi-ply tissue product 10, the overall orientation of the tissue sheets 12 and 12a relative to one another may be varied. However, as polysiloxane treatments are typically applied to improve topical or surface softness of a tissue sheet 12 or finished tissue product 10, one embodiment of a multi-ply tissue product 10 of the present invention has at least one outer surface 30 and/or 32 comprising layers (for example 14 and/or 22 as shown in FIG. 3 or 14 and/or 16 as shown in FIG. 2) comprising the polysiloxane pretreated pulp fibers, thereby placing at least one layer of the tissue sheets 12 and 12a comprising a high or the highest level of polysiloxane outwardly facing so as to be on the outer surface 30 and/or 32 contacting the user's skin.

In another embodiment of the present invention, the tissue product 10 may comprise hardwood and softwood kraft pulp fibers. In other embodiments of the present invention, at least one tissue sheet 12 may comprise hardwood and softwood kraft pulp fibers. It may be desirable in some embodiments for the polysiloxane pretreated pulp fibers to comprise hardwood kraft pulp fibers. It may also be desirable in some embodiments of the present invention to position the polysiloxane pretreated pulp fibers comprised of hardwood kraft pulp fibers in at least one of the outer layers of the tissue sheets 12 that form the outer surfaces 30 and/or 32 of the tissue product 10. In variations of this embodiment of the present invention, the remaining layers of the tissue sheets 12 of the tissue product 10 may or may not comprise polysiloxane pretreated pulp fibers, the order of the layers and/or tissue sheets 12 may be varied in any order. Any number of additional layers and/or tissue sheets 12 may be employed in the tissue product 10 of the present invention. More specifically, according to one embodiment, the tissue product 10 is a single ply product. The tissue sheet 12 has a structure comprised of three layers 14, 16, and 18. The first outer layer 14 comprises polysiloxane pretreated pulp fibers comprised of hardwood kraft pulp fibers, forming the outer surface 30 of the tissue product 10. The inner layer 18 comprises softwood kraft pulp fibers not-pretreated with polysiloxane. The second outer layer 16 comprises non-treated pulp fibers comprised of hardwood kraft pulp fibers, forming the outer surface 32 of the tissue product 10. In another embodiment of the present invention, the tissue sheet 12 has a structure comprised of three layers 14, 16, and 18. The first outer layer 14 comprises polysiloxane pretreated pulp fibers comprised of hardwood kraft pulp fibers, forming the outer surface 30 of the tissue product 10. The inner layer 18 comprises non-treated pulp fibers comprised of hardwood kraft pulp fibers. The second outer layer 16 comprises non-treated pulp fibers comprised of softwood kraft pulp fibers, forming the outer surface 32 of the tissue product 10.

In another embodiment of the present invention, the single ply tissue product 10 may comprise a three-layer tissue sheet 12 wherein the first and second outer layers 14 and 16, as shown in FIG. 2, comprise polysiloxane pretreated pulp fibers and the inner layer 18 comprises non-treated pulp fibers.

In another aspect the present invention, the tissue sheets and/or tissue products comprising the polysiloxane pretreated pulp fibers show an improved hydrophilicity without need for layering or secondary application of surfactants. Higher levels of the polysiloxane pretreated pulp fibers may be incorporated into the tissue sheets and/or tissue products of the present invention may therefore be used to supply additional softness benefits to those tissue products.

One particular aspect of the polysiloxane pretreated tissue sheets and/or tissue products of the present invention is that the polysiloxane pretreated tissue sheets and/or tissue products may contain high levels of polydialkylsiloxanes yet the polysiloxane pretreated pulp fibers of the tissue sheet and/or tissue product are capable of retaining both the polydialkylsiloxane, as measured by silicone retention factor, and their hydrophilic character, as measured by the aged water drop test, through broke repulping processes. These characteristics can be determined by measuring the polydialkylsiloxane content and wet out time of the polysiloxane pretreated tissue sheets and/or tissue products by the methods noted hereinafter, repulping the polysiloxane pretreated tissue sheet and/or tissue product and preparing handsheets from 100% of the repulped tissue pulp fibers and measuring both the polydialkylsiloxane content and aged wet out characteristics of the handsheets made from the repulped tissue pulp fibers.

In another aspect of the present invention, the polysiloxane pretreated tissue sheets and/or tissue products may have a polydialkylsiloxane content of greater than about 0.2 to greater than about 2%. In another aspect of the present invention, the polysiloxane pretreated tissue sheets and/or tissue products may have a silicone retention factor of about 60% or greater. In another aspect of the present invention, the polysiloxane pretreated tissue sheets and/or tissue products may have a silicone retention factor of about 75% or greater. In another aspect of the present invention, the polysiloxane pretreated tissue sheets and/or tissue products may have a silicone retention factor of about 90% or greater.

Pulp Fibers:

A wide variety of natural and synthetic pulp fibers are suitable for use in the tissue sheets and/or tissue products of the present invention. The pulp fibers may include fibers formed by a variety of pulping processes, such as kraft pulp, sulfite pulp, thermomechanical pulp, etc. In addition, the pulp fibers may consist of any high-average fiber length pulp, low-average fiber length pulp, or mixtures of the same. Any of the natural pulp fibers species may be pretreated with the polysiloxane of the present invention.

One example of suitable high-average length pulp fibers includes softwood kraft pulp fibers. Softwood kraft pulp fibers are derived from coniferous trees and include pulp fibers such as, but not limited to, northern softwood, southern softwood, redwood, red cedar, hemlock, pine (e.g., southern pines), spruce (e.g., black spruce), combinations thereof, and the like. Northern softwood kraft pulp fibers may be used in the present invention. One example of commercially available northern softwood kraft pulp fibers suitable for use in the present invention include those available from Kimberly-Clark Corporation located in Neenah, Wis. under the trade designation of "Longlac-19".

Low-average length fibers are often used to increase the softness of a tissue sheet and/or tissue product. An example of suitable low-average length pulp fibers are the so called hardwood kraft pulp fibers. Hardwood kraft pulp fibers are derived from deciduous trees and include pulp fibers such as, but not limited to, eucalyptus, maple, birch, aspen, and the like. In certain instances, eucalyptus kraft pulp fibers may be particularly desired to increase the softness of the tissue sheet. Eucalyptus kraft pulp fibers may also enhance the brightness, increase the opacity, and change the pore structure of the tissue sheet to increase its wicking ability. Moreover, if desired, secondary pulp fibers obtained from recycled materials may be used, such as fiber pulp from sources such as, for example, newsprint, reclaimed paperboard, and office waste.

In some embodiments of the present invention, the polysiloxane pretreated pulp fibers may be comprised of hardwood kraft pulp fibers, of softwood kraft pulp fibers, or a blend of hardwood and softwood kraft pulp fibers. In one embodiment of the present invention, the length of the polysiloxane pretreated pulp fibers may be of low average length and comprising hardwood kraft pulp fibers. In some embodiments, the polysiloxane pretreated pulp fibers may be of a single species such as eucalyptus, maple, birch, aspen or blends of various hardwood pulp fiber species thereof. In some embodiments of the present invention where a layered tissue sheet is employed, at least one outer layer (such as 14 and/or 16 as shown in FIG. 2 and 14 and/or 22 as shown in FIG. 3) may be comprised of polysiloxane pretreated pulp fibers comprised primarily of hardwood kraft pulp fibers. In other layered tissue sheet embodiments of the present invention, the outer layers (such as 14 and/or 16 as shown in FIG. 2 and 14 and/or 22 as shown in FIG. 3) may be comprised of polysiloxane pretreated pulp fibers comprised of hardwood kraft pulp fibers which may be blended with softwood kraft pulp fibers that may be polysiloxane pretreated pulp fibers, non-treated pulp fibers, or a blend of polysiloxane pretreated pulp fibers and non-treated pulp fibers. In some embodiments of the present invention, if present, the amount of softwood kraft pulp fibers (polysiloxane pretreated or non-treated) in the layer containing the polysiloxane pretreated pulp fibers will be about 20% or less by weight of the total dry pulp fiber in the layer, about 15% or less by weight of the total dry pulp fiber in the layer, or about 10% or less by weight of the total dry pulp fiber in the layer. In another embodiment of the present invention, the polysiloxane pretreated pulp fibers are hardwood kraft pulp fibers, including northern hardwood kraft pulp fibers and eucalyptus hardwood kraft pulp fibers.

The overall ratio of hardwood kraft pulp fibers to softwood kraft pulp fibers within the tissue product or tissue sheets may vary broadly. However, in some embodiments of the present invention, tissue product may comprise a blend of hardwood kraft pulp fibers and softwood kraft pulp fibers (polysiloxane pretreated pulp fibers and/or non-treated pulp fibers) wherein the ratio of hardwood kraft pulp fibers to softwood kraft pulp fibers is from about 9:1 to about 1:9, more specifically from about 9:1 to about 1:4, and most specifically from about 9:1 to about 1:3. In one embodiment of the present invention, the hardwood kraft pulp fibers and softwood kraft pulp fibers (polysiloxane pretreated pulp fibers and/or non-treated pulp fibers) may be layered so as to give a heterogeneous distribution of hardwood kraft pulp fibers and softwood kraft pulp fibers in the z-direction of the tissue sheet and/or tissue product. In another embodiment, the hardwood kraft pulp fibers (polysiloxane pretreated pulp fibers and/or non-treated pulp fibers) may be located in at least one of the outer layers (the outer layers, such as 14 and/or 16 as shown in FIG. 2 or 14 and/or 22 as shown in FIG. 3 which may form the outer surfaces 30 and 32 of the tissue product 10) of the tissue product 10 wherein at least one of the inner layers may comprise softwood kraft pulp fibers not containing polysiloxane pretreated pulp fibers.

In addition, synthetic fibers may also be utilized. The discussion herein regarding pulp fibers not pretreated with polysiloxane is understood to include synthetic fibers. Some suitable polymers that may be used to form the synthetic fibers include, but are not limited to: polyolefins, such as, polyethylene, polypropylene, polybutylene, and the like; polyesters, such as polyethylene terephthalate, poly(glycolic acid) (PGA), poly(lactic acid) (PLA), poly(β-malic acid) (PMLA), poly(ε-caprolactone) (PCL), poly(ρ-dioxanone) (PDS), poly(3-hydroxybutyrate) (PHB), and the like; and, polyamides, such as nylon and the like. Synthetic or natural cellulosic polymers, including but not limited to: cellulosic esters; cellulosic ethers; cellulosic nitrates; cellulosic acetates; cellulosic acetate butyrates; ethyl cellulose; regenerated celluloses, such as viscose, rayon, and the like; cotton; flax; hemp; and mixtures thereof may be used in the present invention. The synthetic fibers may be located in the layers of the tissue sheet and/or tissue product comprising polysiloxane pretreated pulp fibers, the layers of the tissue sheet and/or tissue product comprising non-treated pulp fibers, or in any or all layers of the tissue sheet and/or tissue product. As discussed for tissue sheets, in multi-ply tissue products of the present invention, the synthetic fibers may be located in any or all tissue sheets of the multi-ply tissue product.

Polysiloxanes:

The particular structure of the polysiloxanes of the present invention may provide the desired tissue product properties to the pulp fibers and tissue sheets and/or tissue products. Polysiloxanes encompass a very broad class of compounds. They are characterized in having a backbone structure:

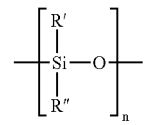

where R' and R" may be a broad range of organo and non-organo groups including mixtures of such groups and where n is an integer $\geq 2$. These polysiloxanes may be linear, branched, or cyclic. They may include a wide variety of polysiloxane copolymers containing various compositions of functional groups, hence, R' and R" actually may represent many different types of groups within the same polymer molecule. The organo or non-organo groups may be capable of reacting with pulp fibers to covalently, ionically or hydrogen bond the polysiloxane to the pulp fibers. These functional groups may also be capable of reacting with themselves to form crosslinked matrixes with the pulp fibers. The scope of the present invention should not be construed as limited by a particular polysiloxane structure so long as that polysiloxane structure delivers the aforementioned product benefits to the tissue sheet and/or the final tissue product.

The term "polydialkylsiloxane" as used herein refers to the portion of the polysiloxane molecule as defined above wherein R' and R" are $C_1$–$C_{30}$ aliphatic hydrocarbon groups. In one embodiment of the present invention, R' and R" may be methyl groups forming so called polydimethylsiloxane units. While not wishing to be bound by theory, the polydialkylsiloxane units may be capable of increasing the softness of tissue sheet and/or tissue products comprising polysiloxane pretreated pulp fibers. Functionalized polysiloxanes containing polydialkylsiloxane units may be used for the purposes of the present invention. A variety of functional groups may be present on the polysiloxane polymer in addition to the dialkylsiloxane units. A combination of polysiloxanes may also be used to create the desired tissue sheets and/or tissue products.

A specific class of hydrophobic polysiloxanes suitable for use in the present invention to be blended with the hydrophilic polysiloxane may have the general formula:

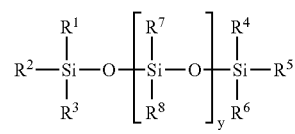

wherein the $R^1$–$R^8$ moieties may be independently any organofunctional group including $C_1$ or higher alkyl groups, aryl groups, ethers, polyethers, polyesters, amines, imines, amides, or other functional groups including the alkyl and alkenyl analogues of such groups and y is an integer >1. Specifically, the $R^1$–$R^8$ moieties may be independently any $C_1$ or higher alkyl group including mixtures of the alkyl groups. Examples of polysiloxanes that may be useful in the present invention are those in the DC-200 fluid series and HMW-2200, manufactured and sold by Dow Corning, Inc., located in Midland, Mich.

Additional examples of hydrophobic polysiloxanes that may be well suited for use in the present invention are the so called amino-functional polysiloxanes. These amino functional polysiloxanes having the following general structure may be useful in the present invention:

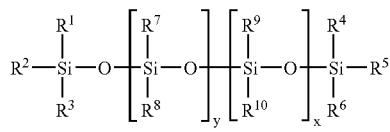

wherein, x and y are integers >0. The mole ratio of x to (x+y) may be from about 0.001 to about 0.25. The $R^1$–$R^9$ moieties may be independently any organofunctional group including $C_1$ or higher alkyl groups, aryl groups, ethers, polyethers, polyesters, amines, imines, amides, or other functional groups including the alkyl and alkenyl analogues of such groups. The $R^{10}$ moiety may be an amino functional moiety including but not limited to primary amine, secondary amine, tertiary amines, quaternary amines, unsubstituted amides and mixtures thereof. In one embodiment, the $R^{10}$ moiety may comprise at least one amine group per constituent or two or more amine groups per substituent, separated by a linear or branched alkyl chain of $C_1$ or greater. Examples of some polysiloxanes that may be useful in the present invention include, but are not limited to, DC 2-8220, DC-8175 and DC-8182 commercially available from Dow Corning, Inc., located in Midland, Mich., Y-14344 commercially available from Crompton, Corp., located at Greenwich, Conn. and AF-23 commercially available from Wacker, Inc., Adrian, Mich.

The polysiloxane pretreated pulp fibers of the present invention incorporate at least one hydrophilic polysiloxane. Such polysiloxanes may be incorporated wholly or in part with other functional polysiloxanes to generate the required hydrophilic properties of the pulp fibers and tissue sheets and/or tissue products. One common class of hydrophilic polysiloxanes is the so called polyether polysiloxanes. Such polysiloxanes generally have the following structure:

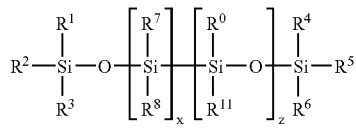

wherein, z is an integer >0 and x is an integer $\geq 0$. The mole ratio of x to (x+z) may be from about 0 to about 0.95. The $R^0$–$R^9$ moieties may be independently any organofunctional group including a $C_1$ or higher alkyl or aryl group or mixtures of such groups. $R^{11}$ may be a polyether functional group having the generic formula: —$R^{12}$—$(R^{13}$—O$)_a$—$(R^{14}O)_b$—$R^{15}$, wherein $R^{12}$, $R^{13}$, and $R^{14}$ may be independently $C_{1-4}$ alkyl groups, linear or branched; $R^{15}$ may be H or a $C_{1-30}$ alkyl group; and, "a" and "b" are integers of from about 1 to about 100, more specifically from about 5 to about 30. An example of a commercially available polyethers polysiloxane is DC-1248 available from Dow Corning. While these polysiloxanes are broadly taught in the art and used in combination with hydrophobic polysiloxanes their use to impart hydrophilicity is precluded in the case of pretreated pulp fibers as will be demonstrated in subsequent examples. The hydrophilic polysiloxanes of this particular structure lack a functional group capable of anchoring the polysiloxane substantively to the pulp fibers. Hence, the polyether polysiloxanes are removed from the polysiloxane pretreated pulp fibers when used in wet laid applications such as tissue or papermaking. Loss of the polyether polysiloxane may cause loss of any or all softness or hydrophilic benefit that the polyether polysiloxane was intended to deliver to the final tissue sheet and/or tissue product made from the polysiloxane pretreated pulp fibers.

A class of functionalized hydrophilic polysiloxanes particularly suitable for use in the present invention are polyether polysiloxanes that include an additional functional group capable of substantively affixing the hydrophilic polysiloxane to the pulp fibers. Thus, the hydrophilic polysiloxane is retained by the polysiloxane pretreated pulp fibers during wet laid papermaking processes. Such polysiloxanes may generally have the following structure:

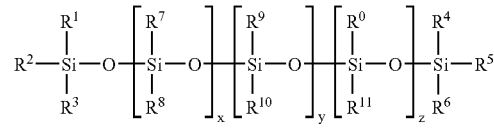

wherein, z is an integers >0, x and y are integers $\geq 0$. The mole ratio of x to (x+y+z) may be from about 0 to about 0.95. The ratio of y to (x+y+z) may be from about 0 to about 0.4. The $R^0$–$R^9$ moieties may be independently any organofunctional group including $C_1$ or higher alkyl groups, aryl groups, ethers, polyethers, polyesters or other functional groups including the alkyl and alkenyl analogues of such groups. The $R^{10}$ moiety is a moiety capable of substantively affixing the polysiloxane to the cellulose. In a specific embodiment of the present invention, the $R^{10}$ moiety is an amino functional moiety including, but not limited to, primary amine, secondary amine, tertiary amines, quaternary amines, unsubstituted amides, and mixtures thereof. An exemplary $R^{10}$ amino functional moiety may contain one amine group per constituent or two or more amine groups per substituent, separated by a linear or branched alkyl chain of $C^1$ or greater. $R^{11}$ may be a polyether functional group having the generic formula: —$R^{12}$—$(R^{13}$—O$)_a$—$(R^{14}O)_b$—$R^{15}$, wherein $R^{12}$, $R^{13}$, and $R^{14}$ may be independently $C_{1-4}$ alkyl groups, linear or branched; $R^{15}$ may be H or a $C_{1-30}$ alkyl group; and, "a" and "b" are integers of from about 1 to about 100, more specifically from about 5 to about 30. Examples of aminofunctional polysiloxanes that may be useful in the present invention include the polysiloxanes provided under the trade designation of Wetsoft CTW family manufactured and sold by Wacker, Inc., located Adrian, Mich. Other examples of such polysiloxanes may be found in U.S. Pat. No. 6,432,270, issued on Aug. 13, 2002 to Liu, et al., U.S. Pat. No. 6,599,393 issued on Jun. 29, 2003 to Liu, et al., U.S. Pat. No.6,511,580 issued on Jan. 28, 2003 to Liu, U.S. Pat. No. 6,514,383 issued on Feb. 4, 2003 to Liu, U.S. Pat. No. 6,235,155 issued on May 22, 2001 to Schroeder, et al., and U.S. Pat. No. 6,632,904 issued on Oct. 14, 2003 to Schroeder, et al., the disclosure of which is incorporated herein by reference to the extent that it is non-contradictory herewith. In another aspect of the present invention, the moiety capable of affixing the polysiloxane substantively to the pulp fiber may be incorporated into the hydrophilic segment of the polysiloxane polymer or on one of the other $R^0$–$R^{11}$ moieties. In such case, the value of y in the above structure for the hydrophilic polysiloxane may be 0.

While the specific amount of the $R^{10}$ or other moiety capable of substantively affixing the polysiloxane to the pulp fibers may be varied in the present invention such that the desired silicone retention factor is met, the amount or nature of substantively affixing groups should be such that the presence of nits is reduced in the tissue sheets and/r tissue products made with the polysiloxane pretreated pulp fibers. These nits are described as fiber/polymer bundles that create the appearance of white spots within the tissue sheet and/or tissue product. These white spots will generally be on the order of one square millimeter in size or greater. The nit count refers to the number of nits counted in a 7.5"×7.5" handsheet prepared from the polysiloxane pretreated pulp fibers. Handsheets made with the polysiloxane pretreated pulp fibers should specifically have a nit count of about 10 or less, more specifically about 5 or less, and still more specifically about 3 or less.

The-hydrophilic polysiloxanes of the present invention may be blended with hydrophobic polysiloxanes on the pulp fibers, thereby providing polysiloxane pretreated pulp fibers wherein the polysiloxane pretreated pulp fibers impart acceptable hydrophilic properties to the tissue sheet and/or tissue product incorporating the polysiloxane pretreated pulp fibers. The ratio of the hydrophobic polysiloxane to hydrophilic polysiloxane used as a treatment may range from about 0:1 to about 9.9:0.1, in another aspect from about 0:1 to about 9:1 and in still another aspect from about 0:1 to about 4:1.

Polysiloxane Pretreated Pulp Fibers:

The preparation of polysiloxane pretreated pulp fibers can be accomplished by methods such as those described in U.S. Pat. No. 6,582,560 issued to Runge, et. al., on Jun. 24, 2003. It has been found that pulp fibers treated with polysiloxane in this manner demonstrate excellent retention of the polysiloxane through the tissue making process. Furthermore, it has been found that a polysiloxane which may be desorbed from the fibers in the tissue making process has little to no tendency to be adsorbed by non-treated pulp fibers. The polysiloxane pretreated pulp fibers may contain from about 0.1% to about 20% polysiloxane by weight, more specifically from about 0.2% to about 10% polysiloxane by weight, and most specifically from about 0.3% polysiloxane to about 5% polysiloxane by weight.

The polysiloxane pretreated pulp fibers may constitute from about 2% to about 100% by weight of the dry pulp fibers basis in the layer of the tissue sheet and/or tissue product comprising the polysiloxane pretreated pulp fibers, more specifically from about 10% to about 100% by weight of the dry pulp fibers in the layer or layers comprising the polysiloxane pretreated pulp fibers, and most specifically from about 15% to about 100% by weight of the dry pulp fibers in the layer comprising the polysiloxane pretreated pulp fibers.

Methods of Application:

The polysiloxanes of the present invention may be applied to pulp fibers in accordance with any method and form so long as the claimed product benefits are not compromised. The polysiloxane may be delivered to the pulp fibers as an aqueous emulsion or dispersion, a solution in an organic fluid or non-organic fluid medium, or as a neat polysiloxane containing no added solvents, emulsifiers, or other agents.

The method by which the polysiloxane may be added to pulp fibers to form the polysiloxane pretreated pulp fibers may be any method known in the art. One method may be to dry the pulp fibers to a consistency of about 95% or greater subsequent to the application of the polysiloxane to the pulp fibers and prior to the pulp fibers being redispersed in water at the tissue machine. The polysiloxane may be added to the pulp fibers at a pulp mill. The pulp fibers may be only once dried prior to the pulp fibers being dispersed during the tissue making process. Other embodiments for adding the polysiloxanes to the pulp fibers include, but are not limited to, processes that incorporate comminuted or flash dried pulp fibers being entrained in an air stream combined with an aerosol or spray of a polysiloxane so as to treat individual pulp fibers prior to incorporation of the polysiloxane pretreated pulp fibers into the tissue sheet and/or tissue product. Other embodiments involving secondary processes may be utilized with the present invention. Examples of such processes include, but are not limited to:

Preparing a slurry of non-treated, once dried pulp fibers, dewatering and drying the non-treated pulp fibers to form a partially dried or dried web of non-treated pulp fibers, treating partially dried or dried web of non-treated pulp fibers with a polysiloxane to form a partially dried or dried polysiloxane pretreated pulp fiber web, further drying said partially dried or dried polysiloxane pretreated pulp fiber web to form a dried polysiloxane pretreated pulp fiber web comprising polysiloxane pretreated pulp fibers.

Applying a polysiloxane directly to a roll of dried or partially dried non-treated pulp fibers to form a roll of polysiloxane pretreated pulp fibers.

It should be understood that while such secondary processes may be used to pretreat the pulp fibers with polysiloxane that utilizing such processes may result in undesirable issues, such as a significant economic penalty to the overall tissue product characteristics or properties.

The application of a polysiloxane to a partially dried or dried pulp fiber web to form the polysiloxane pretreated pulp fibers may be accomplished by any method known in the art including, but not limited to:

Contact printing methods such as gravure, offset gravure, flexographic printing, and the like.

A spray applied to a pulp fiber web. For example, spray nozzles may be mounted over a moving pulp fiber web to apply a desired dose of a solution to the moist pulp fiber web. Nebulizers may also be used to apply a light mist to a surface of a pulp fiber web.

Non-contact printing methods such as ink jet printing, digital printing of any kind, and the like.

Coating onto one or both surfaces of the pulp fiber web, such as blade coating, air knife coating, short dwell coating, cast coating, size presses, and the like.

Extrusion of a polysiloxane from a die head such as UFD spray tips available from ITW Dynatec of Jackson, Tenn., in the form of a solution, a dispersion or emulsion, or a viscous mixture.

Foam application of a polysiloxane to the moist or dry pulp fiber web (e.g., foam finishing), either for topical application or for impregnation of the polysiloxane into the pulp fiber web under the influence of a pressure differential (e.g., vacuum-assisted impregnation of the foam). Principles of foam application of additives such as binder agents are described in U.S. Pat. No. 4,297, 860, issued on Nov. 3, 1981 to Pacifici et al. and U.S. Pat. No. 4,773,110, issued on Sep. 27, 1988 to G. J. Hopkins, the disclosures of both of which are incorporated herein by reference to the extent that they are non-contradictory herewith.

Application of a polysiloxane by spray or other means to a moving belt or fabric which in turn contacts the pulp fiber web to apply the polysiloxane to the pulp fiber web, such as is disclosed in WO 01/49937 under the name of S. Eichhorn, published on Jun. 12, 2001.

Tissue Preparation:

At the tissue machine, the dried polysiloxane pretreated pulp fiber is mixed with water to form at least one pulp fiber slurry of the polysiloxane pretreated pulp fiber wherein the polysiloxane may be retained by the individual pulp fibers pretreated with polysiloxane. Non-treated pulp fibers may also be added to the pulp fiber slurry comprising the polysiloxane pretreated pulp fibers. Any number of optional pulp fiber slurries may be prepared using non-treated or polysiloxane pretreated pulp fibers in the same manner as the pulp fiber slurry comprising polysiloxane pretreated pulp fibers. In one embodiment of the present invention, a pulp fiber slurry comprising the polysiloxane pretreated pulp fibers and at least one pulp fiber slurry comprising non-treated pulp fibers may be passed to a stratified headbox. The pulp fiber slurries may be deposited from the stratified headbox onto a moving wire or belt, wherein the pulp fiber slurry comprising the polysiloxane pretreated pulp fibers may be directed to at least one of the outside layers of the stratified headbox. The pulp fiber slurries are deposited to form a wet layered tissue sheet 12 wherein the polysiloxane pretreated pulp fibers may comprise at least one of the outer layers of the wet tissue sheet 12 (such as outer layers 14 and/or 16 as shown in FIG. 2 or outer layers 14, 16, 20, and/or 22 as shown in FIG. 3). The wet layered tissue sheet 12 may be dewatered, dried, and processed to form a dried tissue sheet 12. The dried tissue sheet 12 may be converted into a tissue product 10.

The tissue sheet 12 to be treated can be made by any method known in the art. The tissue sheet 12 may be wetlaid, such as a tissue sheet 12 formed with known papermaking techniques wherein a dilute aqueous fiber slurry is disposed on a moving wire to filter out the fibers and form an embryonic web which is subsequently dewatered by combinations of units including suction boxes, wet presses, dryer units, and the like. Examples of known dewatering and other operations are given in U.S. Pat. No. 5,656,132, issued on Aug. 12, 1997 to Farrington et al. Capillary dewatering can also be applied to remove water from the web, as disclosed in U.S. Pat. No. 5,598,643 issued on Feb. 4, 1997 and U.S. Pat. No. 4,556,450 issued on Dec. 3, 1985, both to S. C. Chuang et al.

For the tissue sheets and/or tissue products of the present invention, both creped and uncreped methods of manufacture may be used. Uncreped tissue production is disclosed in U.S. Pat. No. 5,772,845, issued on Jun. 30,1998 to Farrington, Jr. et al., the disclosure of which is herein incorporated by reference to the extent it is non-contradictory herewith. Creped tissue production is disclosed in U.S. Pat. No. 5,637,194, issued on Jun. 10, 1997 to Ampulski et al.; U.S. Pat. No. 4,529,480, issued on Jul. 16, 1985 to Trokhan; U.S. Pat. No. 6,103,063, issued on Aug. 15, 2000 to Oriaran et al.; and, U.S. Pat. No. 4,440,597, issued on Apr. 3, 1984 to Wells et al., the disclosures of all of which are herein incorporated by reference to the extent that they are non-contradictory herewith. Also suitable for application of the above mentioned polysiloxanes are tissue sheets and/or tissue products that are pattern densified or imprinted, such as the webs disclosed in any of the following U.S. Pat. No.: 4,514,345, issued on Apr. 30, 1985 to Johnson et al.; U.S. Pat. No. 4,528,239, issued on Jul. 9, 1985 to Trokhan; U.S. Pat. No. 5,098,522, issued on Mar. 24, 1992; U.S. Pat. No. 5,260,171, issued on Nov. 9, 1993 to Smurkoski et al.; U.S. Pat. No. 5,275,700, issued on Jan. 4, 1994 to Trokhan; U.S. Pat. No. 5,328,565, issued on Jul. 12, 1994 to Rasch et al.; U.S. Pat. No. 5,334,289, issued on Aug. 2, 1994 to Trokhan et al.; U.S. Pat. No. 5,431,786, issued on Jul. 11, 1995 to Rasch et al.; U.S. Pat. No. 5,496,624, issued on Mar. 5, 1996 to Steltjes, Jr. et al.; U.S. Pat. No. 5,500,277, issued on Mar. 19, 1996 to Trokhan et al.; U.S. Pat. No. 5,514,523, issued on May 7, 1996 to Trokhan et al.; U.S. Pat. No. 5,554,467, issued on Sep. 10, 1996 to Trokhan et al.; U.S. Pat. No. 5,566,724, issued on Oct. 22, 1996 to Trokhan et al.; U.S. Pat. No. 5,624,790, issued on Apr. 29, 1997 to Trokhan et al.; and, U.S. Pat. No. 5,628,876, issued on May 13, 1997 to Ayers et al., the disclosures of all of which are herein incorporated by reference to the extent that they are non-contradictory herewith. Such imprinted tissue sheets and/or tissue product may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet and/or tissue product superposed over the deflection conduits was deflected by an air pressure differential across the deflection conduit to form a lower-density pillow-like region or dome in the tissue sheet and/or tissue product.

Various drying operations may be useful in the manufacture of the tissue sheets and/or tissue products of the present invention. Examples of such drying methods include, but are not limited to, drum drying, through drying, steam drying such as superheated steam drying, displacement dewatering, Yankee drying, infrared drying, microwave drying, radiofrequency drying in general, and impulse drying, as disclosed in U.S. Pat. No. 5,353,521, issued on Oct. 11, 1994 to Orloff and U.S. Pat. No. 5,598,642, issued on Feb. 4, 1997 to Orloff et al., the disclosures of both which are herein incorporated by reference to the extent that they are non-contradictory herewith. Other drying technologies may be used, such as methods employing differential gas pressure include the use of air presses as disclosed U.S. Pat. No. 6,096,169, issued on Aug. 1, 2000 to Hermans et al. and U.S. Pat. No. 6,143,135, issued on Nov. 7, 2000 to Hada et al., the disclosures of both which are herein incorporated by reference to the extent they are non-contradictory herewith. Also relevant are the paper machines disclosed in U.S. Pat. No. 5,230,776, issued on Jul. 27, 1993 to I. A. Andersson et al.

Optional Chemical Additives:

Optional chemical additives may also be added to the aqueous pulp fiber slurries of the present invention and/or to the embryonic tissue sheet and/or tissue product to impart additional benefits to the tissue sheet and/or tissue product and process and are not antagonistic to the intended benefits of the present invention. The following chemical additives are examples of additional chemical treatments that may be applied to the tissue sheets and/or tissue products comprising the polysiloxane pretreated pulp fibers. The chemical additives are included as examples and are not intended to limit the scope of the present invention. Such chemical additives may be added at any point in the papermaking process, before or after the formation of the tissue sheet and/or tissue product. The chemical additives may also be added with the polysiloxane during the pretreatment of pulp fibers thereby forming the polysiloxane pretreated pulp fibers, therefore the chemical additives may be added in conjunction with the polysiloxane pretreated pulp fibers. Optionally, the chemical additives may be applied to the pulp fibers during the pulping process that are not pretreated with polysiloxane, thus non-treated pulp fibers.

It is also understood that the optional chemical additives may be employed in specific layers of the tissue sheet and/or tissue product or may be employed throughout the tissue sheet and/or tissue product as broadly known in the art. For example, in a layered tissue sheet configuration, strength agents may be applied only to the layer of the tissue sheet and/or tissue product comprising softwood pulp fibers and/or bulk debonders may be applied only to the layer of the tissue sheet and/or tissue product comprising hardwood pulp fibers. While significant migration of the chemical additives into the other untreated layers of the tissue sheet and/or tissue product may occur, benefits may be further realized than when the chemical additives are applied to all layers of the tissue sheet and/or tissue product on an equal basis. Such layering of the optional chemical additives may be useful in the present invention.

Charge Control Agents:

Charge promoters and control agents are commonly used in the papermaking process to control the zeta potential of the papermaking furnish in the wet end of the process. These species may be anionic or cationic, most usually cationic, and may be either naturally occurring materials such as alum or low molecular weight high charge density synthetic polymers typically of molecular weight less than 500,000. Drainage and retention aids may also be added to the furnish to improve formation, drainage and fines retention. Included within the retention and drainage aids are microparticle systems containing high surface area, high anionic charge density materials.

Strength Additives:

Wet and dry strength agents may also be applied to the tissue sheet and/or tissue product. As used herein, the term "wet strength agents" are materials used to immobilize the bonds between pulp fibers in the wet state. Typically, the means by which pulp fibers are held together in tissue sheets and tissue products involve hydrogen bonds and sometimes combinations of hydrogen bonds and covalent and/or ionic bonds. In the present invention, it may be useful to provide a material that will allow bonding of pulp fibers in such a way as to immobilize the fiber-to-fiber bond points and make the pulp fibers resistant to disruption in the wet state. In this instance, the wet state usually will mean when the tissue sheet or tissue product is largely saturated with water or other aqueous solutions, but could also mean significant saturation with body fluids such as urine, blood, mucus, menses, runny bowel movement, lymph and other body exudates.

Any material that when added to a tissue sheet or tissue product results in providing the tissue sheet or tissue product with a mean wet geometric tensile strength:dry geometric tensile strength ratio in excess of 0.1 will, for purposes of the present invention, be termed a wet strength agent. Typically these materials are termed either as permanent wet strength agents or as "temporary" wet strength agents. For the purposes of differentiating permanent wet strength agents from temporary wet strength agents, the permanent wet strength agents will be defined as those resins which, when incorporated into tissue sheets or tissue products, will provide a tissue product that retains more than about 50% of its original wet strength after being saturated with water for a period of at least five minutes. Temporary wet strength agents are that provide a tissue product that retains less than about 50% of its original wet strength after being saturated with water for five minutes. Both classes of material may find application in the present invention. The amount of wet strength agent that may be added to the pulp fibers may be about 0.1 dry weight percent or greater, more specifically about 0.2 dry weight percent or greater, and still more specifically from about 0.1 to about 3 dry weight percent, based on the dry weight of the pulp fibers.

Permanent wet strength agents will provide a more or less long-term wet resilience to the structure of a tissue sheet or tissue product. In contrast, the temporary wet strength agents will typically provide tissue sheet or tissue product structures that had low density and high resilience, but would not provide a structure that had long-term resistance to exposure to water or body fluids.

Wet and Temporary Wet Strength Additives:

Temporary wet strength additives may be cationic, non-ionic or anionic. Examples of such temporary wet strength additives include PAREZ™ 631 NC and PAREZ® 725 temporary wet strength resins that are cationic glyoxylated polyacrylamides available from Cytec Industries, located at West Paterson, N.J. These and similar resins are described in U.S. Pat. No. 3,556,932, issued to Coscia et al. and U.S. Pat. No. 3,556,933, issued to Williams et al. Hercobond 1366, manufactured by Hercules, Inc. located at Wilmington, Del. is another commercially available cationic glyoxylated polyacrylamide that may be used with the present invention. Additional examples of temporary wet strength additives include dialdehyde starches such as Cobond 1000® commercially available from National Starch and Chemical Company and other aldehyde containing polymers such as those described in U.S. Pat. No. 6,224,714, issued on May 1, 2001 to Schroeder et al.; U.S. Pat. No. 6,274,667, issued on Aug. 14, 2001 to Shannon et al.; U.S. Pat. No. 6,287,418, issued on Sep. 11, 2001 to Schroeder et al.; and, U.S. Pat. No. 6,365,667, issued on Apr. 2, 2002 to Shannon et al., the disclosures of all of which are herein incorporated by reference to the extent that they are non-contradictory herewith.

Permanent wet strength agents comprising cationic oligomeric or polymeric resins may be used in the present invention. Polyamide-polyamine-epichlorohydrin type resins such as KYMENE 557H sold by Hercules, Inc. located at Wilmington, Del. are the most widely used permanent wet-strength agents and are suitable for use in the present invention. Such materials have been described in the following U.S. Pat. No. 3,700,623, issued on Oct. 24, 1972 to Keim; U.S. Pat. No. 3,772,076, issued on Nov. 13, 1973 to Keim; U.S. Pat. No. 3,855,158, issued on Dec. 17, 1974 to Petrovich et al.; U.S. Pat. No. 3,899,388, issued on Aug. 12, 1975 to Petrovich et al.; U.S. Pat. No. 4,129,528, issued on Dec. 12, 1978 to Petrovich et al.; U.S. Pat. No. 4,147,586, issued on Apr. 3, 1979 to Petrovich et al.; and, U.S. Pat. No. 4,222,921, issued on Sep. 16, 1980 to van Eenam. Other cationic resins include polyethylenimine resins and aminoplast resins obtained by reaction of formaldehyde with melamine or urea. Permanent and temporary wet strength resins may be used together in the manufacture of tissue sheets and tissue products with such use being recognized as falling within the scope of the present invention.

Dry Strength Additives:

Dry strength resins may also be applied to the tissue sheet without affecting the performance of the disclosed polysiloxanes of the present invention. Such materials may include, but are not limited to, modified starches and other polysaccharides such as cationic, amphoteric, and anionic starches and guar and locust bean gums, modified polyacrylamides, carboxymethylcellulose, sugars, polyvinyl alcohol, chitosan, and the like. Such dry strength additives are typically added to the pulp fiber slurry prior to the formation of the tissue sheet or as part of the creping package.

Additional Softness Additives:

It may be desirable to add additional debonders or softening chemistries to a tissue sheet. Such softness additives may be found to further enhance the hydrophilicity of the finished tissue product. Examples of debonders and softening chemistries may include the simple quaternary ammonium salts having the general formula $(R^{1'})_{4-b}$—$N^+$—$(R^{1''})_b$ $X^-$ wherein $R^{1'}$ is a $C_{1-6}$ alkyl group, $R^{1''}$ is a $C_{14}$–$C_{22}$ alkyl group, b is an integer from 1 to 3 and $X^-$ is any suitable counterion. Other similar compounds may include the monoester, diester, monoamide, and diamide derivatives of the simple quaternary ammonium salts. A number of variations on these quaternary ammonium compounds should be considered to fall within the scope of the present invention. Additional softening compositions include cationic oleyl imidazoline materials such as methyl-1-oleyl amidoethyl-2-oleyl imidazo linium methylsulfate commercially available as Mackernium CD-183 from McIntyre Ltd., located in University Park, Ill. and Prosoft TQ-1003 available from Hercules, Inc. Such softeners may also incorporate a humectant or a plasticizer such as a low molecular weight polyethylene glycol (molecular weight of about 4,000 daltons or less) or a polyhydroxy compound such as glycerin or propylene glycol. These softeners may be applied to the pulp fibers while in a pulp fiber slurry prior to the formation of a tissue sheet and/or tissue product to aid in bulk softness.

Miscellaneous Agents:

Additional types of chemical additives that may be added to the tissue sheet include, but is not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin e and the like may also be incorporated into the tissue sheet and/or tissue product.

In general, the polysiloxane pretreated pulp fibers of the present invention may be used in conjunction with any known materials and chemical additives that are not antagonistic to their intended use. Examples of such materials include, but are not limited to, odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like. A wide variety of other materials and chemical additives known in the art of tissue-making production may be included in the tissue sheets of the present invention.

The application point for these materials and chemical additives is not particularly relevant to the invention and such materials and chemical additives may be applied at any point in the tissue manufacturing process. This includes pretreatment of pulp, application in the wet end of the process, post-treatment after drying but on the tissue machine and topical post-treatment.

Analytical Methods

Total Polysiloxane in Sheet

The total polysiloxane content on the pulp fiber substrates was determined using the following procedure. A sample of pure dimethylpolysiloxane is placed in a headspace vial, boron trifluoride reagent is added, and the vial sealed. After reacting for about fifteen minutes at about 100° C., the resulting Diflourodimethyl siloxane in the headspace of the vial is measured by gas chromatography using an FID detector.

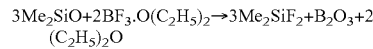

$$3Me_2SiO + 2BF_3.O(C_2H_5)_2 \rightarrow 3Me_2SiF_2 + B_2O_3 + 2(C_2H_5)_2O$$

The method described herein was developed using a Hewlett-Packard Model 5890 Gas Chromatograph with an FID and a Hewlett-Packard 7964 autosampler. An equivalent gas chromatography system may be substituted.

The instrument was controlled by, and the data collected using, Perkin-Elmer Nelson Turbochrom software (version 4.1). An equivalent software program may be substituted. A J&W Scientific GSQ (30 m×0.53 mm i.d.) column with film thickness 0.25 μm, Cat. # 115-3432 was used. An equivalent column may be substituted.

The gas chromatograph was equipped with a Hewlett-Packard headspace autosampler, HP-7964 and set up at the following conditions:

| | |
|---|---|
| Bath Temperature: 100° C. | Loop Temperature: 110° C. |
| Transfer Line Temperature: 120° C. | GC Cycle Time: 25 minutes |
| Vial Equilibrium Time: 15 minutes | Pressurize Time: 0.2 minutes |
| Loop Fill Time: 0.2 minutes | Loop Equil. Time: 0.05 minutes |
| Inject Time: 1.0 minute | Vial Shake: 1 (Low) |

The Gas Chromatograph was set to the following instrument conditions:

Carrier gas: Helium
Flow rate: 16.0 mL through column and 14 mL make-up at the detector.
Injector Temperature: 150° C.
Detector Temperature: 220° C.
Chromatography Conditions:
50° C. for 4 minutes with a ramp of 10° C./minute to 150° C.
Hold at final temperature for 5 minutes.
Retention Time: 7.0 min. for DFDMS A stock solution containing approximately 5000 μg/ml of the polysiloxane being applied was prepared in the following manner. Approximately 1.25 grams of the polysiloxane or polysiloxane emulsion is weighed to the nearest 0.1 mg into a 250-ml volumetric flask. The actual weight (represented as X) is recorded. Distilled water is added and the flask swirled to dissolve/disperse the emulsion. When dissolved/dispersed, the emulsion is diluted to volume with water and mixed. The ppm of the polysiloxane emulsion (represented as Y) is calculated from the following equation:

$$PPM \text{ polysiloxane emulsion } Y = X/0.250$$

The Calibration Standards are made to bracket the target concentration by adding 0 (blank), 50, 100, 250, and 500 μL of the Stock Solution (the volume in uL $V_c$ recorded) to successive 20 mL headspace vials containing 0.1±0.001 grams of an untreated control tissue sheet. The solvent is evaporated by placing the headspace vials in an oven at a temperature ranging between about 60 to about 70° C. for 15 minutes. The μg of emulsion (represented as Z) for each calibration standard is calculated from the following equation:

$$Z = Vc * Y/1000$$

The calibration standards are then analyzed according to the following procedure: 0.100±0.001 g sample of a tissue sheet is weighed to the nearest 0.1 mg into a 20-ml headspace vial. The sample weight (represented as $W_s$) in mg is recorded. The amount of tissue sheet taken for the standards and samples must be the same.

100 μL of $BF_3$ reagent is added to each of the tissue sheet samples and calibration standards. Each vial is sealed immediately after adding the $BF_3$ reagent.

The sealed vials are placed in the headspace autosampler and analyzed using the conditions described previously, injecting 1 mL of the headspace gas from each tissue sheet sample and calibration standard.

A calibration curve of μg emulsion versus analyte peak area is prepared.

The analyte peak area of the tissue sheet sample is then compared to the calibration curve and amount of polysiloxane emulsion (represented as (A)) in μg on the tissue sheet determined.

The amount of polysiloxane emulsion (represented as (C)) in percent by weight on the tissue sample is computed using the following equation:

$$(C) = (A)/(W_s * 10^4)$$

The amount of the polysiloxane (represented as (D)) in percent by weight on the tissue sheet sample is computed using the following equation and the weight % polysiloxane (represented as (F)) in the emulsion:

$$(D) = (C)*(F)/100$$

Polydialkylsiloxane Content

The polydimethylsiloxane content on cellulose fiber substrates was determined using the following procedure. A sample containing polydimethylsiloxane is placed in a headspace vial, boron trifluoride reagent is added, and the vial sealed. After reacting for about fifteen minutes at about 100° C., the resulting Diflourodimethyl siloxane in the headspace of the vial is measured by gas chromatography with an FID detector.

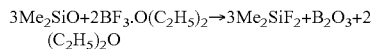

$$3Me_2SiO + 2BF_3 \cdot O(C_2H_5)_2 \rightarrow 3Me_2SiF_2 + B_2O_3 + 2(C_2H_5)_2O$$

The method described herein was developed using a Hewlett-Packard Model 5890 Gas Chromatograph with an FID and a Hewlett-Packard 7964 autosampler. An equivalent gas chromatography system may be substituted.

The instrument was controlled by, and the data collected using, Perkin-Elmer Nelson Turbochrom software (version 4.1). An equivalent software program may be substituted. A J&W Scientific GSQ (30 m×0.53 mm i.d.) column with film thickness 0.25 μm, Cat. # 115-3432 was used. An equivalent column may be substituted.

The gas chromatograph was equipped with a Hewlett-Packard headspace autosampler, HP-7964 and set up at the following conditions:

| | |
|---|---|
| Bath Temperature: 100° C. | Loop Temperature: 110° C. |
| Transfer Line Temperature: 120° C. | GC Cycle Time: 25 minutes |
| Vial Equilibrium Time: 15 minutes | Pressurize Time: 0.2 minutes |
| Loop Fill Time: 0.2 minutes | Loop Equil. Time: 0.05 minutes |
| Inject Time: 1.0 minute | Vial Shake: 1 (Low) |

The gas chromatograph was set to the following instrument conditions:
Carrier gas: Helium
Flow rate: 16.0 mL through column and 14 mL make-up at the detector.
Injector Temperature: 150° C.
Detector Temperature: 220° C.

Chromatography Conditions:
50° C. for 4 minutes with a ramp of 10° C./minute to 150° C.
Hold at final temperature for 5 minutes.
Retention Time: 7.0 min. for DFDMS Preparation of Stock Solution The method is calibrated to pure PDMS using DC-200 fluid available from Dow Corning, Midland, Mich. A stock solution containing about 1250 μg/ml of the DC-200 fluid is prepared in the following manner. About 0.3125 grams of the DC-200 fluid is weighed to the nearest 0.1 mg into a 250-ml volumetric flask. The actual weight (represented as X) is recorded. A suitable solvent such as methanol, MIBK or chloroform is added and the flask swirled to dissolve/disperse the fluid. When dissolved the solution is diluted to volume with solvent and mixed. The ppm of dimethylpolysiloxane (represented as Y) is calculated from the following equation:

$$PPM\ of\ dimethylpolysiloxane\ (Y) = X/0.250$$

Preparation of Calibration Standards

The Calibration Standards are made to bracket the target concentration by adding 0 (blank), 50, 100, 250, and 500 μL of the Stock Solution (the volume in uL $V_c$ recorded) to successive 20 mL headspace vials containing 0.1±0.001 grams of an untreated control tissue web or tissue product. The solvent is evaporated by placing the headspace vials in an oven at a temperature ranging between about 60° C. to about 70° C. for about 15 minutes. The μg of dimethylpolysiloxane (represented as Z) for each calibration standard is calculated from the following equation:

$$Z = Vc * Y/1000$$

Analytical Procedure

The calibration standards are then analyzed according to the following procedure: 0.100±0.001 g of tissue sample is weighed to the nearest 0.1 mg into a 20-ml headspace vial. The sample weight (represented as $W_s$) in mg is recorded. The amount of tissue web and/or tissue product taken for the standards and samples must be the same.

100 μL of $BF_3$ reagent is added to each of the samples and calibration standards. Each vial is sealed immediately after adding the $BF_3$ reagent.

The sealed vials are placed in the headspace autosampler and analyzed using the conditions described previously, injecting 1 mL of the headspace gas from each tissue sample and standard.

Calculations

A calibration curve of μg dimethylpolysiloxane versus analyte peak area is prepared.

The analyte peak area of the tissue sample is then compared to the calibration curve and amount of polydimethylsiloxane (represented as (A)) in μg on the tissue web and/or tissue product is determined.

The amount of polydimethylsiloxane (represented as (C)) in percent by weight on the tissue sample is computed using the following equation:

$$(C)=(A)/(W_s*10^4)$$

The amount of the polydimethylsiloxane (represented as (D)) in percent by weight on the tissue sample is computed using the following equation:

$$(D)=(C)/100$$

When polydialkylsiloxanes other than dimethylpolysiloxane are present, calibration standards are made from representative samples of the pure polydialkylsiloxanes that are present and the amount of each polydialkylsiloxane is determined as in the method above for polydimethylsiloxane. The sum of the individual polydialkylsiloxane amounts is then used for the total amount of polydialkylsiloxane present in the tissue web and/or tissue product.

Basis Weight Determination (Tissue)

The basis weight and bone dry basis weight of the tissue sheet specimens was determined using a modified TAPPI T410 procedure. As is basis weight samples were conditioned at 23° C.±1° C. and 50±2% relative humidity for a minimum of 4 hours. After conditioning a stack of 16—3"× 3" samples was cut using a die press and associated die. This represents a tissue sheet sample area of 144 in². Examples of suitable die presses are TMI DGD die press manufactured by Testing Machines, Inc. located at Islandia, N.Y., or a Swing Beam testing machine manufactured by USM Corporation, located at Wilmington, Mass. Die size tolerances are +/−0.008 inches in both directions. The specimen stack is then weighed to the nearest 0.001 gram on a tared analytical balance. The basis weight in pounds per 2880 ft² is then calculated using the following equation:

$$\text{Basis weight} = \text{stack wt. In grams}/454*2880$$

The bone dry basis weight is obtained by weighing a sample can and sample can lid to the nearest 0.001 grams (this weight is A). The sample stack is placed into the sample can and left uncovered. The uncovered sample can and stack along with sample can lid is placed in a 105° C.±2° C. oven for a period of 1 hour ±5 minutes for sample stacks weighing less than 10 grams and at least 8 hours for sample stacks weighing 10 grams or greater. After the specified oven time has lapsed, the sample can lid is placed on the sample can and the sample can removed from the oven. The sample can is allowed to cool to approximately ambient temperature but no more than 10 minutes. The sample can, sample can lid, and sample stack are then weighed to the nearest 0.001 gram (this weight is C). The bone dry basis weight in pounds/2880 ft² is calculated using the following equation:

$$\text{Bone Dry } BW=(C-A)/454*2880$$

Dry Tensile (Tissue)

The Geometric Mean Tensile (GMT) strength test results are expressed as grams-force per 3 inches of sample width. GMT is computed from the peak load values of the MD (machine direction) and CD (cross-machine direction) tensile curves, which are obtained under laboratory conditions of 23.0° C.±1.0° C., 50.0±2.0% relative humidity, and after the tissue sheet has equilibrated to the testing conditions for a period of not less than four hours. Testing is conducted on a tensile testing machine maintaining a constant rate of elongation, and the width of each specimen tested was 3 inches. The "jaw span" or the distance between the jaws, sometimes referred to as gauge length, is 2.0 inches (50.8 mm). The crosshead speed is 10 inches per minute (254 mm/min.) A load cell or full-scale load is chosen so that all peak load results fall between 10 and 90 percent of the full-scale load. In particular, the results described herein were produced on an Instron 1122 tensile frame connected to a Sintech data acquisition and control system utilizing IMAP software running on a "486 Class" personal computer. This data system records at least 20 load and elongation points per second. A total of 10 specimens per sample are tested with the sample mean being used as the reported tensile value. The geometric mean tensile is calculated from the following equation:

$$GMT=(MD \text{ Tensile}*CD \text{ Tensile})^{1/2}$$

To account for small variations in basis weight, GMT values were then corrected to the 18.5 pounds/2880 ft² target basis weight using the following equation:

$$\text{Corrected } GMT=\text{Measured } GMT*(18.5/\text{Bone Dry Basis Weight})$$

Wet Out Time

The Wet Out Time of a tissue sheet treated in accordance with the present invention is determined by cutting 20 sheets of the tissue sheet sample into 2.5 inch squares. The number of sheets of the tissue sheet sample used in the test is independent of the number of plies per sheet of the tissue sheet sample. The 20 square sheets of the tissue sheet sample are stacked together and stapled at each corner to form a pad of the tissue sheet sample. The pad of the tissue sheet sample is held close to the surface of a constant temperature distilled water bath (23° C.±2° C.), which is the appropriate size and depth to ensure the saturated pad of the tissue sheet sample does not contact the bottom of the water bath container and the top surface of the distilled water of the water bath at the same time, and dropped flat onto the surface of the distilled water, with staple points on the pad of the tissue sheet sample facing down. The time necessary for the pad of the tissue sheet sample to become completely saturated, measured in seconds, is the Wet Out Time for the tissue sheet sample and represents the absorbent rate of the tissue sheet sample. Increases in the Wet Out Time represent a decrease in absorbent rate of the tissue sheet sample. The test is stopped at 300 seconds with any sheet not wetting out in that period given a value of about 300 seconds or greater.

Caliper

The term "caliper" as used herein is the thickness of a single tissue sheet, and may either be measured as the thickness of a single tissue sheet or as the thickness of a stack of ten tissue sheets and dividing the ten tissue sheet thickness by ten, where each sheet within the stack is placed with the same side up. Caliper is expressed in microns. Caliper was measured in accordance with TAPPI test methods T402 "Standard Conditioning and Testing Atmosphere For Paper, Board, Pulp Handsheets and Related Products" and T411 om-89 "Thickness (caliper) of Paper, Paperboard, and Combined Board" optionally with Note 3 for stacked tissue sheets. The micrometer used for carrying out T411 om-89 is a Bulk Micrometer (TMI Model 49-72-00, Amityville, N.Y.) or equivalent having an anvil diameter of $4\frac{1}{16}$ inches (103.2 millimeters) and an anvil pressure of 220 grams/square inch (3.3 g kilo Pascals).

Sensory Softness

Sensory softness is an assessment of tissue sheet in-hand feel softness. This panel is lightly trained so as to provide assessments closer to those a consumer might provide. The strength lies in its generalizability to the consumer population. This softness measure is employed when the purpose is to obtain a holistic overview of attributes of the tissue sheets and to determine if differences in the tissue sheets are humanly perceivable.

The following is the specific softness procedure the panelists utilize while evaluating sensory softness for bath, facial and towel products. Samples of tissue sheets or tissue products are placed across the non-dominant arm with the coded side facing up. The pads of the thumb, index, and middle fingers of the dominant hand are then moved in a circular motion lightly across several areas of the sample. The velvety, silky, and fuzzy feel of the samples of the tissue sheets or tissue products is evaluated. Both sides of the samples are evaluated in the same manner. The procedure is then repeated for each additional sample in a paired comparison analysis.

The sensory softness data results are analyzed using a Freidman Two-Way Analysis of Variance (ANOVA) by Ranks. This analysis is a non-parametric test used for ranking data. The purpose is to determine if there is a difference between different experimental treatments. If there is not a ranking difference between the different experimental treatments, it is reasoned that the median response for one treatment is not statistically different than the median response of the other treatment, or any difference is caused by chance. The difference between the samples can be reported in terms of a preference of one code over another as a ratio of 100. For example, when comparing a sample vs. a control the softness preference can be expressed in terms of x/y where x is the number of respondents out of 100 that would state x is softer than y and y is the number of respondents out of 100 that would state y is softer than x in a paired comparison test.

Sensory softness is assessed by between 10 to 12 panelists applying a rank order paradigm with no replications. For each individual attribute, approximately 24–72 data points are generated. A maximum of six codes may be ranked at one time. More codes may be assessed in multiple studies; however, a control code should be present in each study to provide a common reference if codes are to be compared across multiple studies.

Panel Softness

Softness of tissue sheets and/or tissue products is determined from sensory panel testing. The testing is performed by trained panelists who rub the formed tissue sheets and/or tissue products and compare the various softness attributes of the tissue sheets and/or tissue products to the same softness attributes of high and low softness control standards. Three softness parameters are evaluated a) stiffness, b) fuzzy and c) gritty. After comparing these characteristics to the standards, the panelists assign a value for each of the tissue sheets' and/or tissue products' softness attributes relative to the control standards. The higher the number, the more of the attribute the tissue sheet and/or tissue product possesses. Relative to softness, lower values for stiffness and gritty are preferred while higher numbers are preferred for the fuzzy attribute. Samples are analyzed for statistical significance and in addition to the numerical rating are given a letter value to determine if significantly different from one another. For example, an (a) value would be statistically different at the 95% confidence level from a (b) value. All values rated as (a) would not be statistically different although a difference in numerical value indicates a directional preference.

Water Drop Test

Initial water drop values are measured after conditioning the samples at 23.0° C.±1.0° C., 50.0±2.0% relative humidity for a period of at least 4 hours. Aged water drop values are measured after aging the handsheets at 85° C. in a forced air convection oven for a period of one hour. After aging the samples are cooled and conditioned at 23.0° C.±1.0° C., 50.0±2.0% relative humidity for a period of at least 4 hours.

A 2"×2" sample or larger of the aged or conditioned handsheet is cut from the handsheet. The actual dimension is not critical so long as the entire area is not wet out upon absorption of the water drop. The test sample is placed on a dry, non-porous surface such as a lab bench or flat acrylic or glass plate. 100 microliters, 0.1±0.01 ml. of distilled water (23.0° C.±1.0° C.) is dispensed immediately from an Eppendorf style pipet positioned slightly above the surface of the test specimen. The drop should be positioned close to the center of the specimen. The water drop is viewed on a plane horizontal to the surface of the test specimen. A stopwatch is started immediately after the water is dispensed onto the test specimen. The time in seconds for the water drop to completely be absorbed by the sample is determined by recording the time it takes for the water drop to completely disappear into the horizontal direction, that is, there is no vertical element to the water drop when viewed from the horizontal plane of the sample. This time is referred to as the water drop test value. The procedure is repeated 3 times and the average time recorded for the water drop test value. If after 3 minutes the sample is not completely absorbed the test is stopped and the time recorded as >3 minutes.

Handsheet Preparation 50 grams of the chemically treated pulp was soaked for 5 minutes in approximately 2-liters of tap water and then dispersed for 5 minutes in a British Pulp Disintegrator such as available from Lorentzen and Wettre, Atlanta, Ga. As an alternative, two liters of an approximately 2.5% consistency of the slurry of the pulped silicone pretreated fibers can be used if it is necessary to use more than 25 grams of fibers. The slurry is then diluted with water to a volume of 8 liters (0.625% consistency) and mixed with a mechanical stirrer at moderate agitation for a period of 5 minutes. Handsheets were made with a basis weight of 60 gsm. During handsheet formation, the appropriate amount of fiber (0.625% consistency) slurry required to make a 60 gsm sheet was measured into a graduated cylinder. The slurry was then poured from the graduated cylinder into an 8.5-inch by 8.5-inch Valley handsheet mold (Valley Laboratory Equipment, Voith, Inc.) that had been pre-filled to the appropriate level with water. After pouring the slurry into the mold, the mold was then completely filled with water, including water used to rinse the graduated cylinder. The slurry was then agitated gently with a standard perforated mixing plate that was inserted into the slurry and moved up and down seven times, then removed. The water was then drained from the mold through a wire assembly at the bottom of the mold that retains the fibers to form an embryonic tissue sheet and/or tissue product. The forming wire is a 90×90 mesh, stainless-steel wire cloth. The tissue sheet and/or tissue product is couched from the mold wire with two blotter papers placed on top of the tissue sheet and/or tissue product with the smooth side of the blotter contacting the tissue sheet and/or tissue product.

The blotters are removed and the embryonic tissue sheet and/or tissue product is lifted with the lower blotter paper, to which it is attached. The lower blotter is separated from the other blotter, keeping the embryonic tissue sheet and/or tissue product attached to the lower blotter. The blotter is positioned with the embryonic tissue sheet and/or tissue product face up, and the blotter is placed on top of two other dry blotters. Two more dry blotters are also placed on top of the embryonic tissue sheet and/or tissue product. The stack of blotters with the embryonic tissue sheet and/or tissue product is placed in a Valley hydraulic press and pressed for one minute with 100 psi applied to the tissue sheet and/or tissue product. The pressed tissue sheet and/or tissue product was removed from the blotters and placed on a Valley steam dryer containing steam at 2.5 psig pressure and heated for 2 minutes, with the wire-side surface of the tissue sheet and/or tissue product next to the metal drying surface and a felt under tension on the opposite side of the tissue sheet and/or tissue product. Felt tension was provided by a 17.5 lbs of weight pulling downward on an end of the felt that extends beyond the edge of the curved metal dryer surface. The dried handsheet is trimmed to 7.5 inches square with a paper cutter.

EXAMPLES

For Examples 1 through 14 pretreated pulp fiber was prepared according to one of the following procedures. All silicones were added as neat fluids or, where noted, fluids in low Mw silicone diluents.

200 grams of crumb pulp, on an oven dried basis, consisting of Eucalyptus Hardwood Kraft fibers and having a consistency of 70% was added to a Hobart mixer. Two to four grams of silicone solids (1%–2% by weight of dry fibers) was slowly added to the pulp while mixing. The silicone and pulp combination was mixed for 30 minutes in the Hobart mixer. After the 30 minutes of mixing the sample was spread out on a shallow glass pan and placed in a fume hood for 2 weeks to air dry. The treated, dried and aged crumb pulp samples were tested for total silicone content and % polydimethylsiloxane using the GC-BF$_3$ method outlined above. After aging 60 g/m² handsheets were prepared according to the procedure outlined above. Retention factors were then obtained by analyzing the handsheets for total silicone content and % polydimethylsiloxane using the GC-BF$_3$ method outlined above. Nit values, initial and aged water drop test values were also obtained on the handsheets.

A fully bleached eucalyptus pulp fiber slurry with a pH value of 4.5 was formed into a mat at a basis weight of 150 grams oven-dry pulp per square meter, pressed and dried to at least about 85 percent solids. Next, the corresponding neat polydimethylsiloxane was applied as a spray or stream onto the fiber mat. Silicone was pumped through a peristaltic pump into an application header. The header consisted of a copper pipe with nine outlet valves. Addition rate was controlled by changing the pump speed and the number of outlet valves open. Machine speed was 18 ft/min, with silicone applied at 4.4 –5.0 ml/min. The amount of the chemical applied to the mat was approximately 1.5% by weight of dried eucalyptus pulp fiber. The pulp fiber samples were then allowed to age at ambient conditions for 2-weeks.

After two weeks the treated, dried and aged pulp fiber samples were tested for total silicone content and % polydimethylsiloxane using the GC-BF$_3$ method outlined above. Then 60 g/m² handsheets were prepared according to the procedure outlined above. Retention factors were then obtained by analyzing the handsheets for total silicone content and % polydimethylsiloxane using the GC-BF$_3$ method outlined above. Initial and aged water drop test values were then obtained on the handsheets.

Examples 7 and 8 use commercially available hydrophobic, high Mw (250 cps) amino functional polydimethylsiloxane fluids from Dow Corning, Midland, Mich. As Table 1 shows, these polysiloxanes exhibit excellent retention factors but have water drop test values in excess of 3 minutes.

Examples 1 and 14 are examples of commercially available hydrophilic amino functional polysiloxanes available from Dow Corning, Midland, Mich. The materials are believed to be a combination of an epoxy functional polysiloxane and an aminofunctional polyether polysiloxane. Initial water drop value and retention factor are good. The 8600 fluid, however, shows significantly more sensitivity to aging.

Example 2 is a combination of a hydrophobic aminofunctional polysiloxane and a low molecular weight polyether polysiloxane wetting fluid both available from Dow Corning. As shown in the table the initial and aged water drop values exceed 3 minutes. Example 3 is the low molecular weight non-aminofunctional wetting fluid, DC-193. This fluid does not have a group capable of substantively affixing the polysiloxane to the cellulose fibers. As shown in the Table 1, this polysiloxane has a poor retention factor.

Example 6 is a high viscosity non-amino functional polyether polysiloxane. As such this material does not contain a group capable of substantively affixing the polysiloxane to the cellulose fibers. The material exhibits a very poor retention factor. Example 3 is a high viscosity epoxy functional polyether that is non-amino functional. Good hydrophilic properties are noted but the retention factor is poor.

Example 9 is an example of a commercially available aminofunctional polyether polydimethylsiloxane terpolymer, Wetsoft CTW, available from Wacker, Inc., located in Adrian, Mich. The material demonstrates an excellent retention factor and excellent initial and aged water drop test values. Comparing this result to the result of Examples 4 and 6, shows the-importance of having a group capable of substantively affixing the hydrophilic polysiloxane to the pulp fibers. As Wetsoft CTW is rather highly substituted, the level of polydialkylsiloxane is somewhat low as a percent of total silicone. Examples 10 through 13 show the utility of combining the high Mw amino functional polyether polysiloxane with a high Mw hydrophobic aminofunctional polysiloxane. Polysiloxane-pretreated pulp fibers having high levels of polydialkylsiloxane, yet having good initial and aged water drop test values are achieved using the combination. Note the improved performance of this material over the use of the non-amino functional wetting fluid of Example 2.

TABLE 1

| Ex. | Silicone | Initial silicone added to pulp (% by wt. dry fiber) | Retention Factor | Silicone Type | Initial water drop test | Aged water drop test 1 hour @ 85° C. | Polydialkyl siloxane content |
|---|---|---|---|---|---|---|---|
| 1 | 8600 | 1% | 0.65 | Epoxy polyether plus amino functional polysiloxane | 5 sec. | >3 min | — |
| 2 | Q2-8220/DC 193, 4:1 | 1% | 0.7 | Amino functional fluid plus silicone wetting agent. | >3 min. | >3 min | 0.65 |
| 3 | 193 | 1% | 0.2 | Polysiloxane wetting agent/surfactant | 0 s | 0 s | <0.1 |
| 4 | 8421 | 1% | 0.30 | Non-amino functional silicone polyether with epoxy functional groups | 3 s | 3 s | <0.2 |
| 5 | 8813 | 1% | 0.45 | Amido polysiloxane fluid. | 5 s | >3 min | — |
| 6 | 1248 | 1% | 0.15 | Polyether polysiloxane no amino functionality | Immediate | 2 s | <0.1 |
| 7 | Q2-8220 | 1% | 0.70 | Amino functional polydialkyl siloxane + 20% cyclodimethicone | >3 min | >3 min | 0.7 |
| 8 | Q2-8175 | 1.2% | 0.83 | Aminofunctional polydimethyl polysiloxane | >3 min. | >3 min | 0.98 |
| 9[1] | Wetsoft CTW | 1.3% | 0.82 | Aminofunctional polyether polysiloxane with polydialkylsiloxane units | 0 sec. | 0 sec. | 0.40 |
| 10 | 90% (8) + 10% (9) | 1.2% | 1.0 | Aminofunctional polydimethyl siloxane plus aminofunctional polyether polysiloxane | >3 min. | >3 min. | 0.94 |
| 11[1] | 70% (8) + 30% (9) | 1.2% | 1.0 | Aminofunctional polydimethyl siloxane plus aminofunctional polyether polysiloxane | 10 sec. | 130 sec. | 0.82 |
| 12[1] | 50% (8) + 50% (9) | 1.1% | 1.0 | Aminofunctional polydimethyl siloxane plus aminofunctional polyether polysiloxane | 7 sec. | 15 sec. | 0.70 |
| 13[1] | 30% (8) + 70% (9) | 1.1% | 1.0 | Aminofunctional polydimethyl siloxane plus aminofunctional polyether polysiloxane | 2 sec. | 3 sec. | 0.58 |
| 14[1] | DC-8500 | 1.1% | 0.73 | Amino/epoxy functional polyether. | 4 sec. | 35 sec. | 0.65 |

[1]Invention

Examples 15–18

Examples 15–18 demonstrate the use of the pretreated pulp in manufacture of a 2-ply facial tissue product and comparison to a control sample not containing the pretreated pulp fiber. Even at low addition levels the addition of the polysiloxane pretreated pulp fiber is found to provide a significant increase in softness and that the hydrophilic polysiloxane pretreated pulp fiber is as efficacious as the hydrophobic polysiloxane pretreated pulp fiber.

The tissue sheet was manufactured according to the following procedure. Polysiloxane pretreated pulp fiber (containing from about 1.0–1.5% polysiloxane) was blended with untreated Eucalyptus pulp fiber in a ratio sufficient to give a total polysiloxane content in the sheet of 0.2% by weight of dry pulp fibers. The treated and non-treated Eucalyptus pulp fibers were dispersed in a pulper for 30 minutes, forming an eucalyptus hardwood pulp kraft fiber slurry having a consistency of about 3%. The Eucalyptus hardwood pulp fiber slurry was then transferred to a machine chest and diluted to a consistency of about 0.75%.

LL-19 northern softwood kraft pulp fibers were dispersed in a pulper for 30 minutes, forming a northern softwood kraft pulp fiber slurry having a consistency of 3%. A low level of refining was applied for 6 minutes to the softwood kraft pulp fibers. After dispersing, the northern softwood draft pulp fibers to form the slurry, the northern softwood kraft pulp fibers were passed to a machine chest and diluted to a consistency of about 0.75%. 1.8 pounds per ton of a commercially available glyoxylated PAM, Parez 631NC was added to the softwood pulp fibers in the machine chest and allowed to mix for 5 minutes prior to forwarding to the headbox.

Kymene 6500, a commercially available PAE wet strength resin from Hercules, Inc., was added to both the eucalyptus hardwood and northern softwood kraft pulp fiber slurries in the machine chest at a rate of 4 pounds of dry chemical per ton of dry pulp fiber.

The stock pulp fiber slurries were further diluted to approximately 0.1 percent consistency prior to forming and deposited from a three layered headbox onto a fine forming fabric having a velocity of about 50 feet per minute to form a 17" wide tissue sheet. The flow rates of the stock pulp fiber slurries into the flow spreader were adjusted to give a target tissue sheet basis weight of about 12.7 gsm and a layer split of 32.5% Eucalyptus hardwood kraft pulp fibers on the dryer and felt side layers and 35% LL-19 northern softwood kraft pulp fibers in the center layer. The stock pulp fiber slurries were drained on the forming fabric, building a layered embryonic tissue sheet. The embryonic tissue sheet was transferred to a second fabric, a papermaking felt, before being further dewatered with a vacuum box to a consistency of between about 15 and about 25%. The embryonic tissue sheet was then transferred via a pressure roll to a steam heated Yankee dryer operating at a temperature of 220° F. at a steam pressure of 17 PSI. The dried tissue sheet was then transferred to a reel traveling at a speed 30% slower than the Yankee dryer to provide a crepe ratio of 1.3:1, thereby providing the layered tissue sheet and/or tissue product.

An aqueous creping composition was prepared containing 0.635% by weight of polyvinyl alcohol (PVOH), available under the trade designation of Celvol 523 manufactured by Celanese (88% hydrolyzed with a viscosity of 23–27 cps. for a 6% solution at 20° C.) and 0.05% by weight of a PAE resin, available under the trade designation of Kymene 6500 from Hercules, Inc. All weight percentages are based on dry pounds of the chemical being discussed. The creping composition was prepared by adding the specific amount of each chemical to 50 gallons of water and mixing well. PVOH was obtained as a 6% aqueous solution and Kymene 557 as a 12.5% aqueous solution. The creping composition was then applied to the Yankee dryer surface via a spray boom at a pressure of 60 psi at a rate of approximately 0.25 g solids/m² of tissue product. The finished layered tissue sheet was then converted into a 2-ply c-folded tissue product with the dryer side layer of each ply facing outward.

Table 2 compares the sensory and panel values of a control with no polysiloxane, the hydrophobic polysiloxane, the hydrophilic polysiloxane and a 50/50 w/w blend of hydrophobic and hydrophilic polysiloxane. As Table 2 indicates, sensory softness shows all codes to be significant for softness relative to the control standard. There is, however, no statistically significant difference in the softness of the 3 codes containing the polysiloxane pretreated pulp fiber. Panel softness attributes (Stiffness, Fuzzy, Gritty) show significant improvement at the 95% confidence level for stiffness and fuzzy attributes with the polysiloxane pretreated pulp fibers. No difference is seen in numerical values for gritty on the samples.

TABLE 2

| Example | Polysiloxane | Sensory Softness Preference | Panel Stiffness | Panel Fuzzy | Panel Gritty |
|---|---|---|---|---|---|
| 15 | None | — | 4.3 (a) | 6.5 (a) | 1.3 (a) |
| 16 | DC-8175 | 72/28 | 3.6 (b) | 7.0 (b) | 1.3 (a) |
| 17 | Wetsoft CTW | 77/23 | 4.0 (a) | 7.0 (b) | 1.3 (a) |
| 18 | 50/50 blend of Wetsoft CTW and DC-8175 | 74/26 | 3.6 (b) | 6.9 (b) | 1.3 (a) |

While the embodiments of the present invention described herein are presently preferred, various modifications and improvements may be made without departing from the spirit and scope of the present invention. The scope of the present invention is indicated by the appended claims, and all changes that fall within the meaning and range of equivalents are intended to be embraced therein.

We claim:

1. Polysiloxane pretreated pulp fibers comprising:
   a) pulp fibers; and,
   b) a hydrophobic polysiloxane; and
   c) a hydrophilic polysiloxane;
wherein the polysiloxane pretreated pulp fibers have a polydialkylsiloxane content of about 0.4 percent by weight of dry fibers or greater, a silicone retention factor of about 0.6 or greater and an initial water drop absorption value of about 180 second or less.

2. The polysiloxane pretreated pulp fibers of claim 1, wherein the polydialkylsiloxane content is about 0.6 percent by weight of dry pulp fibers or greater.

3. The polysiloxane pretreated pulp fibers of claim 1, wherein the polydialkylsiloxane content is about 0.8 percent by weight of dry pulp fibers or greater.

4. The polysiloxane pretreated pulp fibers of claim 1, wherein the initial water drop absorption value is about 30 seconds or less.

5. The polysiloxane pretreated pulp fibers of claim 1, wherein the initial water drop absorption value is about 10 seconds or less.

6. The polysiloxane pretreated pulp fibers of claim 1, wherein the polysiloxane pretreated pulp fibers further comprises non-treated pulp fibers.

7. The polysiloxane pretreated pulp fibers of claim 1, wherein the polysiloxane pretreated pulp fibers are once dried.

8. The polysiloxane pretreated pulp fibers of claim 1, wherein the hydrophobic polysiloxane is a functional polysiloxane having the general structure of:

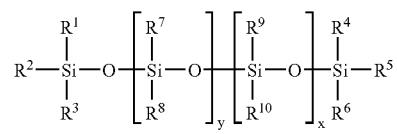

wherein:
   x and y are integers >0;
   the mole ratio of x to (x+y) is from about 0.001 to about 0.25;
   each $R^1$–$R^9$ moiety comprises independently an organofunctional group or mixtures thereof; and,
   $R^{10}$ comprises a functional moiety capable of substantively affixing the polysiloxane to the pulp fibers.

9. The polysiloxane pretreated pulp fibers of claim 8, wherein each $R^1$–$R^9$ moiety comprises independently a $C_1$ or higher alkyl group, aryl group, ester, substituted amide, or mixture thereof.

10. The polysiloxane pretreated pulp fibers of claim 8, wherein the $R^{10}$ moiety comprises en amino functional moiety.

11. The polysiloxane pretreated pulp fibers of claim 10, wherein the amino functional moiety is selected from a primary amine, secondary amine, tertiary amine, quaternary amine, unsubstituted amide, and mixtures thereof.

12. The polysiloxane pretreated pulp fibers of claim 10, wherein the $R^{10}$ moiety is —$R^{20}$—NH—$R^{21}$—$NH_2$ where $R^{20}$ and $R^{21}$ are $C_2$ or higher linear or branched alkyl groups.

13. The polysiloxane pretreated pulp fibers of claim 1, wherein the hydrophilic polysiloxane is has a general structure of:

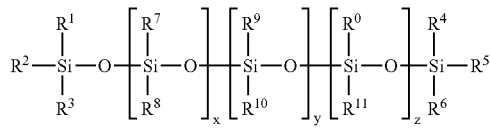

wherein:
- z is an integer >0;
- x and y are integers $\geq 0$;
- the mole ratio of x to (x+y+z) is from about 0 to about 0.95;
- the mole ratio of y to (x+y+z) is from about 0 to about 0.25;
- each $R^0$–$R^9$ comprises independently an organofunctional group or mixtures thereof;
- $R^{10}$ comprises a functional moiety or mixtures thereof capable of substantively affixing the polysiloxane to the pulp fibers; and,
- $R^{11}$ comprises a hydrophilic functionality wherein if y=0 then one of the $R^0$–$R^{11}$ moieties contains a functional group capable of substantively affixing the polysiloxane to the pulp fibers.

14. The polysiloxane pretreated pulp fibers of claim 13, wherein each $R^0$–$R^9$ moiety comprises independently a $C_1$ or higher alkyl group, aryl group, ether, polyether or polyester group, or mixtures thereof.

15. The polysiloxane pretreated pulp fibers of claim 13, wherein each $R^7$ and $R^8$ is $CH_3$.

16. The polysiloxane pretreated pulp fibers of claim 13, wherein $R^{10}$ comprises an amino functional moiety selected from a primary amine, secondary amine, tertiary amine, quaternary amine, unsubstituted amide, and mixtures thereof.

17. The polysiloxane pretreated pulp fibers of claim 13, wherein $R^{11}$ comprises a polyether functional group having the formula: —$R^{12}$—$(R^{13}$—O$)_a$—$(R^{14}O)_b$—$R^{15}$ wherein:
- each $R^{12}$, $R^{13}$, and $R^{14}$ comprises independently branched $C_{1-4}$ alkyl groups, linear $C_{1-4}$ alkyl groups, or mixtures thereof;
- $R^{15}$ comprises H, $C_{1-30}$ alkyl group, or mixtures thereof; and,
- a and b are integers of from about 1 to about 100.

18. The polysiloxane pretreated pulp fibers of claim 1, wherein each polysiloxane has a viscosity at 25° C. of about 25 centipoise or greater.

19. The polysiloxane pretreated pulp fibers of claim 1, wherein each polysiloxane has a viscosity at 25° C. of about 200 centipoise or greater.

20. The polysiloxane pretreated pulp fibers of claim 1, wherein the pulp fibers are selected from the group consisting essentially of: softwood kraft pulp fibers; hardwood kraft pulp fibers; synthetic cellulosic fibers: or, mixture thereof.

21. The polysiloxane pretreated pulp fibers of claim 1, wherein the pulp fibers comprise hardwood kraft pulp fibers.

22. The polysiloxane pretreated pulp fibers of claim 1, wherein the polysiloxane pretreated pulp fibers have a water drop test value of about 180 seconds or less after aging at 85° C. for 24 hours.

23. The polysiloxane pretreated pulp fibers of claim 1, wherein the polysiloxane pretreated pulp fibers have a water drop test value of about 30 seconds or less after aging at 85° C. or 24 hours.

24. The polysiloxane pretreated pulp fibers of claim 1, wherein the polysiloxane pretreated pulp fibers have a nit count of about 10 or less.

25. The polysiloxane pretreated pulp fibers of claim 1, wherein the polysiloxane pretreated pulp fibers have a nit count of about 2 or less.

26. A single or multi-ply tissue product containing the polysiloxane pretreated pulp fibers of claim 1.

27. A wiping product containing the polysiloxane pretreated pulp fibers of claim 1.

28. The single or multi-ply tissue product of claim 26, wherein the tissue product containing the polysiloxane pretreated pulp fibers comprises blended sheets.

29. The single or multi-ply tissue product of claim 26, wherein the tissue product containing the polysiloxane pretreated pulp fibers comprises layered tissue sheets.

30. The single or multi-ply tissue product of claim 26, wherein the tissue product is a facial tissue, a bath tissue, or a towel product.

31. The single or multi-ply tissue product of claim 26, wherein the tissue product has a polydialkylsiloxane content of about 0.15% by weight of dry pulp fibers or greater.

* * * * *